United States Patent
DeRosa et al.

(10) Patent No.: US 10,137,087 B2
(45) Date of Patent: *Nov. 27, 2018

(54) LIPID-DERIVED NEUTRAL NANOPARTICLES

(71) Applicant: TRANSLATE BIO, INC., Lexington, MA (US)

(72) Inventors: Frank DeRosa, Chelmsford, MA (US); Braydon Charles Guild, Concord, MA (US); Michael Heartlein, Boxborough, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/878,137

(22) Filed: Jan. 23, 2018

(65) Prior Publication Data
US 2018/0169016 A1    Jun. 21, 2018

Related U.S. Application Data

(63) Continuation of application No. 14/389,165, filed as application No. PCT/US2013/034604 on Mar. 29, 2013, now Pat. No. 9,877,919.
(Continued)

(51) Int. Cl.
*A61K 9/12* (2006.01)
*A61K 9/127* (2006.01)
(Continued)

(52) U.S. Cl.
CPC .......... *A61K 9/1277* (2013.01); *A61K 9/1271* (2013.01); *A61K 9/1272* (2013.01);
(Continued)

(58) Field of Classification Search
CPC .................................................. A61K 9/1277
See application file for complete search history.

(56) References Cited

U.S. PATENT DOCUMENTS

| 4,737,323 A | 4/1988 | Martin et al. |
| 4,897,355 A | 1/1990 | Eppstein et al. |

(Continued)

FOREIGN PATENT DOCUMENTS

| DE | 3728917 A1 | 3/1989 |
| WO | WO-1998/51278 | 11/1998 |

(Continued)

OTHER PUBLICATIONS

U.S. Appl. No. 61/494,714.
(Continued)

*Primary Examiner* — Benjamin J Packard
(74) *Attorney, Agent, or Firm* — Proskauer Rose LLP; Fangli Chen

(57) ABSTRACT

Disclosed herein are novel lipids and liposomal compositions prepared using such compounds and related methods of neutralizing or otherwise modifying such liposomal compositions. The lipids described herein are useful for example, as liposomal vehicles to facilitate the delivery of encapsulated polynucleotides to target cells and the subsequent transfection of such target cells. In certain embodiments, one or more of the compounds that comprise the liposomal delivery vehicle may be neutralized or further modified such that the properties of the liposomal delivery vehicle are modified.

22 Claims, 2 Drawing Sheets

Specification includes a Sequence Listing.

Related U.S. Application Data

(60) Provisional application No. 61/617,478, filed on Mar. 29, 2012.

(51) Int. Cl.
    *C12N 15/11*     (2006.01)
    *A61K 38/44*     (2006.01)
    *A61K 47/28*     (2006.01)
    *A61K 48/00*     (2006.01)

(52) U.S. Cl.
    CPC .............. *A61K 38/44* (2013.01); *A61K 47/28* (2013.01); *C12N 15/111* (2013.01); *A61K 48/00* (2013.01); *C12N 2310/11* (2013.01); *C12N 2310/14* (2013.01); *C12N 2310/141* (2013.01); *C12N 2310/16* (2013.01); *C12N 2310/3515* (2013.01); *C12N 2320/32* (2013.01); *C12Y 113/12007* (2013.01)

(56) References Cited

U.S. PATENT DOCUMENTS

| | | |
|---|---|---|
| 5,171,678 A | 12/1992 | Behr et al. |
| 5,194,654 A | 3/1993 | Hostetler et al. |
| 5,223,263 A | 6/1993 | Hostetler et al. |
| 5,334,761 A | 8/1994 | Gebeyehu et al. |
| 5,744,335 A | 4/1998 | Wolff et al. |
| 5,885,613 A | 3/1999 | Holland et al. |
| 5,965,434 A | 10/1999 | Wolff et al. |
| 6,153,434 A | 11/2000 | Hughes et al. |
| 6,379,698 B1 | 4/2002 | Leamon |
| 7,005,140 B2 | 2/2006 | Zhang |
| 8,936,942 B2 | 1/2015 | Heyes et al. |
| 8,999,351 B2 | 4/2015 | Manoharan et al. |
| 8,999,950 B2 | 4/2015 | MacLachlan et al. |
| 9,018,187 B2 | 4/2015 | Heyes et al. |
| 9,074,208 B2 | 7/2015 | MacLachlan et al. |
| 9,717,690 B2 | 8/2017 | Guild et al. |
| 9,877,919 B2 | 1/2018 | DeRosa et al. |
| 2003/0082154 A1 | 5/2003 | Leamon |
| 2003/0083272 A1 | 5/2003 | Wiederholt et al. |
| 2009/0270481 A1 | 10/2009 | MacLachlan et al. |
| 2011/0092739 A1 | 4/2011 | Chen et al. |
| 2014/0288160 A1 | 9/2014 | Guild et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0086614 A1 | 3/2015 | Bancel et al. |
| 2015/0111248 A1 | 4/2015 | Bancel et al. |
| 2015/0265708 A1 | 9/2015 | Manoharan et al. |
| 2018/0008543 A1 | 1/2018 | Guild et al. |
| 2018/0161451 A1 | 6/2018 | Fotin-Mleczek et al. |
| 2018/0169020 A1 | 6/2018 | Guild et al. |

FOREIGN PATENT DOCUMENTS

| | | |
|---|---|---|
| WO | WO-2000/064484 A2 | 11/2000 |
| WO | WO-2001/05375 A1 | 1/2001 |
| WO | WO-2005/0121348 A1 | 12/2005 |
| WO | WO-2007/031091 A2 | 3/2007 |
| WO | WO-2010/042877 A1 | 4/2010 |
| WO | WO-2011/039144 A1 | 4/2011 |
| WO | WO-2011/068810 A1 | 6/2011 |
| WO | WO-2012/170889 A1 | 12/2012 |
| WO | WO-2013/090186 A1 | 6/2013 |
| WO | WO-2013/151669 A1 | 10/2013 |
| WO | WO-2015/006747 A2 | 1/2015 |
| WO | WO-2015/011633 A1 | 1/2015 |

OTHER PUBLICATIONS

U.S. Appl. No. 61/494,745.
U.S. Appl. No. 61/494,881.
U.S. Appl. No. 61/494,882.
U.S. Appl. No. 15/878,131, filed Jan. 23, 2018, DeRosa et al.
Anchordoquy, T.J. and Koe, G.S., Physical Stability of Nonviral Plamid-Based Therapeutics, J. Pharm. Sci., 89:289-296 (2000).
Behr, J.P. et al., Efficient gene transfer into mammalian primary endocrine cells with lipopolyamine-coated DNA, Proc. Nat'l Acad. Sci., 86(18): 6982-6986 (1989).
Bloomfield, V.A., Quasi-elastic light scattering applications in biochemistry and biology, Ann. Rev. Biophys. Bioeng., 10: 421-450 (1981).
Budker, V. et al., Protein/Amphipathic Polyamine ComplexesEnable Highly Efficient Transfection withMinimalToxicity, BioTechniques, 23: 139-147 (1997).
Caplen, N.J. et al., In vitro liposome-mediated DNA transfection of epithelial cell lines using the cationic liposome DC-Chol/DOPE, Gene Ther., 2(9): 603-613 (1995).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N'',N'''-Tetraacetic Acid (DOTA)-Peptide versus 2IT-DOTA Monoclonal Antibody Linkage for RIT1, Clin. Cancer Res., 9: 3665s (2003).
Fechter, P. et al., Recognition of mRNA cap structures by viral and cellular proteins, J. Gen. Virology, 86(5): 1239-1249 (2005).
Felgner, P.L. et al., Lipofection: a highly efficient, lipid-mediated DNA-transfection procedure, Proc. Nat'l Acad. Sci. 84: 7413 (1987).
Gao, X. and Huang, L., A novel cationic liposome reagent for efficient transfection of mammalian cells, Biochem. Biophys. Res. Comm., 179(1): 280-285 (1991).
Guttman, M. et al., Chromatin signature reveals over a thousand highly conserved large non-coding RNAs in mammals, Nature, 458: 223-227 (2009).
Heidenreich, O. et al., High activity and stability of hammerhead ribozymes containing 2'-modified pyrimidine nucleosides and phosphorothioates, J. Biol. Chem., 269(3): 2131-2138 (1994).
Heyes, J. et al., Cationic lipid saturation influences intracellular delivery of encapsulated nucleic acids, J. Controlled Release 107(2): 276-287 (2005).
Huang et al., Thiocholesterol-Based Lipids for Ordered Assembly of Bioresponsive Gene Carriers, Molecular Therapy, 11(3): 409-417 (2004).
International Search Report for PCT/US2012/041663, 4 pages (dated Oct. 8, 2012).
International Search Report for PCT/US2013/034604, 4 pages (Jun. 17, 2013).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Klibanov, A.L. et al., Amphipathic polyethyleneglycols effectively prolong the circulation time of liposomes, FEBS Letters, 268(1): 235-237 (1990).
Kozak M., An analysis of 5'-noncoding sequences from 699 vertebrate messenger RNAs, Nucleic Acids Res 15 (20): 8125-48 (1987).
Lasic, D.D. et al., Gelation of liposome interior. A novel method for drug encapsulation., FEBS Lett., 312(2-3): 255-258, (1992).
Li, S. and Huang, L., In vivo gene transfer via intravenous administration of cationic lipid-protamine-DNA (LPD) complexes, Gene Ther., 4(9): 891-900 (1997).
Li, W. et al., Lipid-based nanoparticles for nucleic acid delivery, Pharm Res., 24(3): 438-449 (2007).

(56) References Cited

OTHER PUBLICATIONS

Manjappa et al., Antibody derivatization and conjugation strategies: Application in preparation of stealth immunoliposome to target chemotherapeutics to tumor, Journal of Controlled Release, 150:2-22. (2010).

Monia, B.P. et al., Evaluation of 2'-Modified Oligonucleotides Containing 2'-Deoxy Gaps as Antisense Inhibitors of Gene Expression, J. Biol. Chem., 268: 14514-15222 (1993).

Morrissey, D.V., et al., Potent and persistent in vivo anti-HBV activity of chemically modified siRNAs, Nat. Biotechnol. 23(8): 1003-1007 (2005).

Ng, J.H. et al., LincRNAs join the pluripotency alliance, Nature Genetics 42(12): 1035-1036 (2010).

Nori, A. et al., Tat-conjugated synthetic macromolecules facilitate cytoplasmic drug delivery to human ovarian carcinoma cells, Bioconj. Chern., 14(1): 44-50 (2003).

Pons, M. et al., Liposomes obtained by the ethanol injection method, Int. J. Pharm., 95: 51-56. (1993).

Semple et al., Efficient encapsulation of antisense oligonucleotides in lipid vesicles using iionizable aminolipids: formation of navel small multilamellar vesicle structures, Biochimica et Biophysica Acta, 1510: 152-166 (2001).

Semple, S.C., et al., Rational design of cationic lipids for siRNA delivery, Nature Biotechnology, 28(2): 172-176 (2010).

Sherwood, R.F. Advanced drug delivery reviews: enzyme prodrug therapy, Adv. Drug Del. Rev., 22: 269-288 (1996).

Stern, L. et al., A novel antitumor prodrug platform designed to be cleaved by the endoprotease legumain, Bioconj. Chern., 20: 500-510 (2009).

Tang, Fuxing et al., Introduction of a Disulfide Bond into a Cationic Lipid Enhances Transgene Expression of Plasmid DNA, *Biochemical and Biophysical Research Communications*, 1998, 242, 141-145.

Toki, B.E. et al., Protease-mediated fragmentation of p-amidobenzyl ethers: a new strategy for the activation of anticancer prodrugs, J. Org. Chern., 67(6): 1866-1872 (2002).

Veronese, F.M. et al., PEG-doxorubicin conjugates: influence of polymer structure on drug release, in vitro cytotoxicity, biodistribution, and antitumor activity, Bioconj. Chern, 16(4): 775-784 (2005).

Wetzer, B. et al., Reducible cationic lipids for gene transfer, Biochemical Journal, 356:747-756 (2001).

Written Opinion for PCT/US2012/041663, 7 pages (dated Oct. 8, 2012).

Written Opinion for PCT/US2013/034604, 9 pages (dated Jun. 17, 2013).

Yokoe, H. and Meyer, T. et al., Spatial dynamics of GFP-tagged proteins investigated by local fluorescence enhancement, Nature Biotechnology, 14: 1252-1256 (1996).

Yoneda et al., A cell-penetrating peptidic GRP78 ligand for tumor cell-specific prodrug therapy, Bioorg. Med. Chern. Lett., 18(5): 1632-1636 (2008).

Robinson et al., "Lipid Nanoparticle-Delivered Chemically Modified mRNA Restores Chloride Secretion in Cystic Fibrosis", Molecular Therapy 26(8): 1-13 (2018).

LIPID-DERIVED NEUTRAL NANOPARTICLES

RELATED APPLICATIONS

This application is a continuation of U.S. application Ser. No. 14/389,165, filed Sep. 29, 2014, which is the U.S. National Stage of International Application No. PCT/US2013/034604, filed Mar. 29, 2013, which claims the benefit of U.S. Provisional Application No. 61/617,478, filed on Mar. 29, 2012, the disclosures of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 17, 2018, is named MRT-1061US3_Sequence Listing.txt and is 2,872 bytes in size.

BACKGROUND

The use of liposomal delivery vehicles to facilitate the site-specific delivery of therapeutic agents represents a rapidly emerging field of drug delivery; however, the efficient delivery of therapeutic agents to targeted cells and tissues, as well as the subsequent transfection of such targeted cells and tissues remains a technical challenge. Despite the availability of multiple lipids and liposomal-based delivery systems to facilitate the delivery of therapeutic agents to target cells and tissues, many challenges still exist in both in vivo and in vitro applications. For example, a significant drawback of liposomal-based delivery systems relates to the construction of liposomes that have sufficient stability and the ability of such liposomes to efficiently release their encapsulated contents to targeted cells and tissues.

With respect to the development of liposomal delivery vehicles for use in delivering nucleic acids, the incorporation of cationic lipids as a component of a liposomal vehicle represents an important advancement. Properties of cationic liposomes, which include for example, their stability, size and surface charge, make them ideal carriers for encapsulating and delivering negatively charged nucleic acids to target cells and tissues. The cationic components (e.g., cationic lipids and/or cationic polymers) that comprise such cationic liposomal vehicles facilitate the interaction between the lipid bilayer of the liposome and the negatively charged nucleic acids, and thereby enhance the encapsulation efficiency of such cationic liposomal vehicles. In part due to their positive surface charge, liposomes prepared comprising cationic lipids (e.g., 1,2-dioleoyl-3-trimethylammonium-propane (DOTAP)) have demonstrated an ability to be efficiently loaded with negatively charged nucleic acids and, the use of cationic liposomal vehicles may facilitate the encapsulation of nucleic acids at concentrations that well exceed those which would be achieved using neutral liposomal vehicles. For example, in certain instances, cationic lipid nanoparticle systems may be characterized as having encapsulation efficiencies approaching 100% when loaded with negatively charged nucleic acids. (See, e.g., Li, et al. Pharm Res., 2007, 24: 438-449.)

Many cationic lipids employed to construct such liposomal vehicles however, are generally toxic and accordingly, may be of limited utility, particularly in the quantities necessary to deliver therapeutically effective quantities of their encapsulated contents (e.g., nucleic acids). Further limiting the utility of charged liposomal systems, following their administration to a subject, such charged systems may be rapidly cleared from the systemic circulation and thereby limit their distribution and accumulation in targeted cells and tissues. To overcome the technical challenges associated with the use of cationic liposomal vehicles, the use of multi-component liposomal delivery systems has been employed. In particular, the preparation of liposomal vehicles using ionizable lipids has been employed as a means of modulating the charge of a liposome in response to the changing pH of an environment (e.g., physiological pH) to which the liposome is exposed. Such ionizable lipids therefore accommodate changes in their surface charge, which may be manipulated, for example, to enhance the encapsulation efficiency of the liposome.

Despite the foregoing limitations, and as a result of their ability to facilitate the delivery of encapsulated materials to target cells, liposomal-based vehicles are an attractive carrier for therapeutic agents and remain subject to continued development efforts. While liposomal-based vehicles that comprise a cationic lipid component have shown promising results with regards to encapsulation and stability, there remains a great need for improved liposomal-based delivery systems.

In contrast to charged liposomal-based vehicles, neutral liposomal vehicles are generally characterized as having relatively improved pharmacokinetic properties. However, in part due to the low encapsulation efficiency observed with neutral liposomes, there have been limited studies performed investigating the use of neutral liposomes to deliver therapeutic agents to target cells. There remains a need for novel lipids that incorporate a multi-functional approach for delivering encapsulated nucleic acids and polynucleotides. Particularly needed are lipid nanoparticles that retain some of the beneficial characteristics of both neutral and charged liposomal delivery systems.

SUMMARY

Described herein are novel lipids and liposomal compositions that comprise such lipids. Also disclosed are methods of using such lipids (e.g., cleavable cationic lipids) as a component of a liposomal composition to facilitate the encapsulation of one or more therapeutic agents (e.g., therapeutic polynucleotides) in such liposomal compositions. Methods of preparing neutral liposomal compositions that are characterized as having high encapsulation efficiencies (e.g., relative to traditional neutral liposomal compositions) are also disclosed herein. The novel methods, lipids and compositions described herein employ a multifunctional strategy to facilitate the encapsulation of one or more therapeutic agents into a neutral liposomal composition and the subsequent transfection of one or more target cells with such liposomal composition.

Disclosed herein are novel lipids and related methods of using such lipids to modulate the properties (e.g., surface charge) of for example, liposomal vehicles (e.g., lipid nanoparticles) into which such novel lipids are incorporated. For example, in certain embodiments, the present inventions relate to methods of manipulating a liposomal vehicle (e.g., a lipid nanoparticle) comprising at least one lipid having a releasable polar head-group, such method comprising a step of contacting the liposomal vehicle with one or more agents to cause the release of the polar head-group from the at least one lipid. In some embodiments, upon the release of such polar head-group from the lipid, the surface charge of the remaining liposomal vehicle is modified. For example, following release of the polar head-group from the lipid, the liposomal vehicle may have an overall neutral surface charge (e.g., a net surface charge or zeta potential of about −2.5 to about +2.5 mV). Alternatively, following release of the polar head-group from the lipid, the liposomal vehicle may have an overall negative surface charge (e.g., a net surface charge or zeta potential less than about 25 mV).

In certain embodiments, the lipids disclosed herein generally comprise a polar head-group (e.g., represented as an $R_1$ group) which is bound to a lipophilic tail-group (e.g., represented as an $R_2$ group) by way of a linker group. In some embodiments, the linker group is (or comprises a functional group that is) susceptible to chemical or enzymatic cleavage (e.g., by reduction or by hydrolysis) upon exposure to one or more agents or environments (e.g., upon exposure to an acidic environment or reducing conditions). In one embodiment, the present invention relates to a method of neutralizing or otherwise modifying a liposomal composition. Generally, such liposomal compositions comprise at least one lipid that has a releasable head-group, a tail-group and a cleavable linker group having the structure of formula I:

(I)

wherein $R_1$ is the releasable (polar) head-group and is selected from the group consisting of imidazole, guanidinium, imine, enamine, amino, an optionally-substituted alkyl amino (e.g., an alkyl amino such as dimethylamino) and an optionally-substituted pyridyl (e.g., pyridine or nitropyridyl); wherein $R_2$ is a lipophilic or non-polar group selected from the group consisting of:

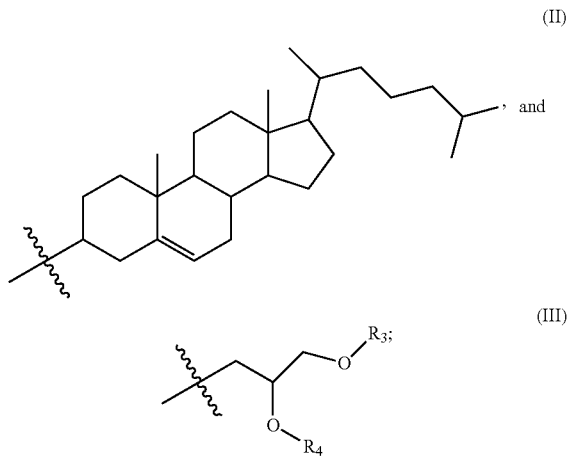

wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; wherein x is a cleavable linker group comprising a functional group selected from the group consisting of a disulfide, ester, hydrazone, imine, acetal, ketal, cis-aconityl, ortho-ester, anhydride, beta-thiopropionate, vinyl ether, phosphoramidate, GLFG, Val-Cit, GG, AA, GGGF and PVGLIG; and wherein n is zero or any positive integer.

In certain embodiments, the methods disclosed herein comprise a step of contacting the lipid or liposomal composition with one or more agents such that the polar head-group ($R_1$) may be cleaved or otherwise liberated from one or more of the cleavable lipids that comprise the liposomal composition (e.g., by reduction of the cleavable linker group), thereby causing the lipophilic $R_2$ group to remain as a component of the liposomal composition. Cleavage and/or release of the polar $R_1$ group from the lipid causes the overall charge of the remaining lipid (and liposomal composition which the lipid is a component) to be modified, and in certain instances causes the liposomal composition to be neutralized.

In certain embodiments, the cleavable linker group is reduced or cleaved and the polar head-group liberated upon contacting the lipid with an agent or environment (e.g., a reducing agent or acidic conditions). Contemplated agents include reducing agents, for example, aqueous solutions comprising one or more of tris (2-carboxyethyl)phosphine (TCEP), β-mercaptoethanol (β-ME), dithiothreitol (DTT), glutathione and dithioerythritol. An appropriate reducing agent may be selected based on the nature of the cleavable linker group that comprises the lipid. For example, a lipid comprising linker group that is susceptible to enzymatic digestion may be contacted with or otherwise exposed to an appropriate enzyme to facilitate cleavage of the polar head-group from the lipid. For example, in certain embodiments such enzymes may include one or more of the enzymes selected from the group consisting of alkaline phosphatase, carboxypeptidase G2, cytosine deaminase, nitroreductase, β-glucuronidase, α-galactosidase, thioredoxin and gamma-interferon inducible lysosomal thiol reductase (GILT). Alternatively, in other embodiments the cleavable linker group may comprise an ester functional group, and the corresponding agent may comprise a compound or agent capable of readily hydrolyzing such ester functional group.

In some embodiments, the degree to which the properties (e.g., surface charge or the average zeta potential) of the liposomal composition are modified is a function of the selected reducing agents to which the liposomal composition is exposed and/or the duration of such exposure. In certain embodiments, the liposomal composition is contacted with the reducing agent from between about five minutes to about twenty four hours (e.g., at least about one minute, two minutes, three minutes, four minutes, five minutes, six minutes, seven minutes, eight minutes, nine minutes, ten minutes, twelve minutes, fifteen minutes, thirty minutes, forty-five minutes, one hour, three hours, six hours, eight hours, twelve hours, sixteen hours, eighteen hours, twenty four hours, or longer). For example, a lipid nanoparticle prepared in accordance with the present invention may have an average zeta potential ($Z_{ave}$) of at least about +25 mV prior to contacting the lipid nanoparticle with the one or more reducing agents. In certain embodiments, the positive charge of the lipid nanoparticle may facilitate encapsulation or loading of one or more therapeutic agents, and in particular negatively charged therapeutic agents (e.g., therapeutic nucleic acids encoding a functional protein or enzyme). For example, the liposomal compositions prepared in accordance with the methods disclosed herein may demonstrate high encapsulation efficiencies (e.g., at least 50%, 55%, 60%, 65%, 70%, 75%, 80%, 85%, 87.5%, 90%, 92.5%, 95%, 97.5%, 98%, 99%, 99.5% or more). Similarly, the liposomal compositions prepared in accordance with the methods disclosed herein may be characterized with respect to the average concentration of one or more therapeutic agents encapsulated in such compositions. For example, in certain embodiments, the average concentration of therapeutic agent encapsulated in a liposomal composition prepared in accordance with the present inventions is between about 0.025 µg/mL to about 250 µg/mL (e.g., at least about 0.05 µg/mL, 0.1 µg/mL, 0.25 µg/mL, 0.5 µg/mL, 1 µg/mL, 2.5 µg/mL, 5 µg/mL, 10 µg/mL, 15 µg/mL, 20 µg/mL, 25 µg/mL, 50 µg/mL, 75 µg/mL, 100 µg/mL, 150 µg/mL, 200 µg/mL, or more).

Once loaded with the one or more therapeutic agents, the physical properties of the liposomal compositions may be further modified. For example, the surface charge of a positively charged liposomal composition (e.g., lipid nanoparticles having a $Z_{ave}$ greater than about +20 mV) may be reduced or neutralized (e.g., reducing the $Z_{ave}$ to less than about +10 mV) based on one or more objectives, such as the characteristics of target cells or tissues. In certain embodiments, the physical properties of the liposomal composition are modulated by contacting the liposomal composition with an aqueous solution comprising one or more reducing agents. Contacting the liposomal composition with such reducing agents causes one or more of the cleavable linker groups of the lipid to be cleaved, resulting in the dissociation of the polar head-group ($R_1$) from the lipophilic group ($R_2$) of the lipid and a corresponding reduction of the $Z_{ave}$ of the remaining liposomal composition. In certain embodiments, after exposure to a reducing agent the $Z_{ave}$ of the liposomal composition is between about +10 mV to about −20 mV (e.g., +10 mV, +7.5 mV, +5 mV, +4 mV, +3 mV, +2.5 mV, +2 mV, +1 mV, +0.5 mV, 0 mV, −0.5 mV, −1 mV, −2 mV, −2.5 mV, −3 mV, −4 mV, −5 mV, −7.5 mV, −10 mV, −12.5 mV, −15 mV or −20 mV). In certain embodiments, after exposure to a reducing agent, the $Z_{ave}$ of the liposomal composition is between about 50 mV to about 5 mV.

The ability to modulate one or more of the physical properties of a liposomal composition (e.g., the ability to reduce the $Z_{ave}$) relates to the composition of the constituent lipids that comprise such composition, and in particular relates to the presence of one or more cleavable linker groups that comprise the constituent lipids that comprise such liposomal composition. In certain embodiments, one or more of the constituent lipids that comprise the liposomal composition comprises a cleavable disulfide (S—S) linker group, as represented, for example, by the following structure:

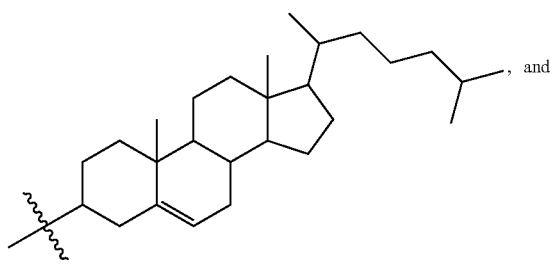

(IV)

wherein $R_1$ is a releasable (polar) head-group selected from the group consisting of imidazole, guanidinium, imine, enamine, amino, an optionally-substituted alkyl amino (e.g., an alkyl amino such as dimethylamino) and an optionally-substituted pyridine or pyridyl (e.g., pyridine or nitropyridyl); wherein $R_2$ is a tail-group selected from the group consisting of:

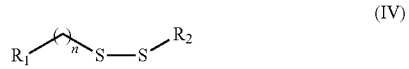

(II)

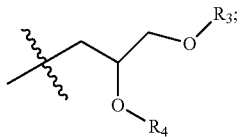

(III)

wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer.

Upon contacting the lipid (or a liposomal composition that comprises such lipid) with one or more agents (e.g., an aqueous solution comprising at least one agent capable of reductively cleaving the disulfide linker group), the disulfide linker group is cleaved from the lipid and a polar group represented by the following structure is liberated:

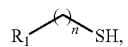

(V)

wherein $R_1$ is the releasable head-group selected from the group consisting of imidazole, guanidinium, imine, enamine, amino, an optionally-substituted alkyl amino (e.g., an alkyl amino such as dimethylamino) and an optionally substituted pyridyl; and the physical properties of the lipid (and the liposomal composition of which the lipid is a component) thereby modified (e.g., neutralized).

In certain embodiments, following exposure of the lipid, and in particular the cleavable disulfide linker group that comprises the lipid, to one or more reducing agents (e.g., β-mercaptoethanol (β-ME)) a thiol group, as represented by the following structure, remains as a component of the liposomal composition:

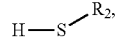

(VI)

wherein $R_2$ is selected from the group consisting of:

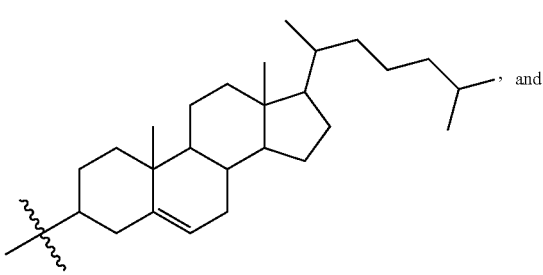

(II)

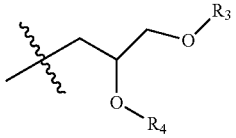

(III)

wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl.

Also disclosed herein are additional means of further modifying the physical and chemical properties of one or more lipids that have been reductively modified or neutralized. In certain embodiments, the sulfhydryl group that comprises the remaining thiol group of the lipid may be further reacted with one or more additional compounds to further modify the physical and/or chemical properties of the reduced liposomal composition. Accordingly, in certain embodiments, after having reductively neutralized the lipid component of the liposomal composition (e.g., a lipid nanoparticle), the remaining sulfhydryl groups coating the external surface of the modified (e.g., neutralized) liposomal composition may be further reacted to introduce additional chemistries or functional groups. For example, the remaining thiol group of the modified or neutral lipid may be contacted or otherwise reacted with a secondary agent, structure or compound represented by the following structure:

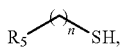

(VII)

wherein $R_5$ is a targeting ligand selected from the group consisting of a peptide, an aptamer, a vitamin and an oligonucleotide. In certain embodiments, the reduced lipid is contacted with the secondary agent or structure under oxidative conditions such that a disulfide bond is formed and the neutral lipid thereby further modified. The modified lipid may be represented by the following structure:

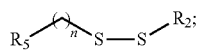

(VIII)

wherein $R_5$ is selected from the group consisting of a polymer (e.g., polyethylene glycol), a peptide, a targeting ligand (e.g., apolipoprotein-B, apolipoprotein-E, glucose, galactose and/or mannose), an alkyl (e.g., an optionally substituted, variably saturated or unsaturated $C_1$-$C_{20}$ alkyl) and a capping structure; wherein n is zero or any positive integer; and wherein $R_2$ is selected from the group consisting of:

(II)

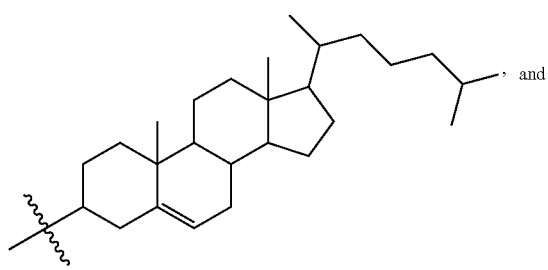, and

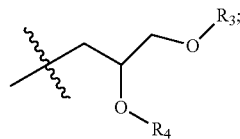

(III)

wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl.

For example, in certain embodiments, the modified lipid may be represented by one of the following structures:

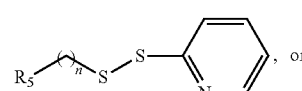, or

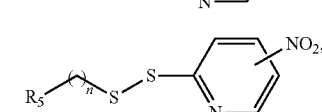

(IX)

(X)

wherein $R_5$ is selected from the group consisting of a polymer (e.g., polyethylene glycol), a peptide, a targeting ligand (e.g., apolipoprotein-B, apolipoprotein-E, glucose, galactose and/or mannose), an alkyl (e.g., an optionally substituted, variably saturated or unsaturated $C_1$-$C_{20}$ alkyl) and a capping structure and wherein n is zero or any positive integer. In other embodiments, the thiol group of a modified or neutral lipid may be contacted or otherwise reacted under suitable conditions (e.g., oxidative conditions) with a secondary agent, structure or compound represented by one or more of the structures (IX) and/or (X) depicted above.

In certain embodiments, the cleavable lipids relate to one or more of the lipid compounds and related methods disclosed in co-owned U.S. Application No. 61/494,745 the contents of which are incorporated herein by reference in their entirety. For example, in some embodiments, the cleavable lipid is the compound 5-(((10,13-dimethyl-17-(6-methylheptan-2-yl)-2,3,4,7,8,9,10,11,12,13,14,15,16,17-tetradecahydro-1H-cyclopenta[a]phenanthren-3-yl)disulfanyl)methyl)-1H-imidazole, having the structure of formula XI (referred to herein as "HGT4001").

(XI)

In some embodiments, the cleavable lipid is the compound 1-(2-(((3S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)disulfanyl)ethyl)guanidine, having the structure of formula XII (referred to herein as "HGT4002").

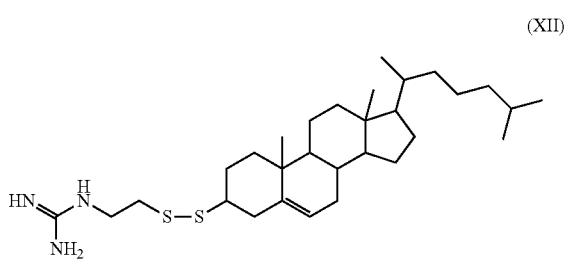 [SMILES: CC(C)CCCC(C)C1CCC2C3CC=C4CC(SSCCNC(=N)N)CCC4(C)C3CCC12C]

(XII)

In some embodiments, the cleavable lipid is the compound 24-(2,3-Bis((9Z,12Z)-octadeca-9,12-dien-1-yloxy)propyl)disulfanyl)-N,N-dimethylethanamine, having the structure of formula XIII (referred to herein as "HGT4003").

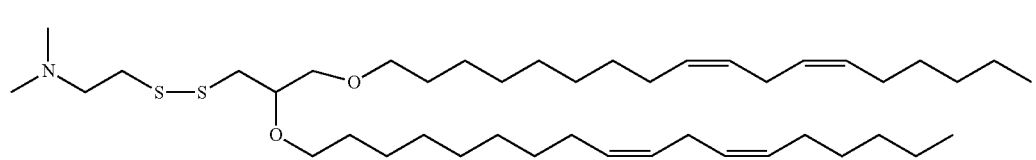

(XIII)

In yet other embodiments, the cleavable lipid is the compound 5-(((2,3-bis((9Z,12Z)-octadeca-9,12-dien-1-yloxy)propyl)disulfanyl)methyl)-1H-imidazole having the structure of formula XIV (referred to herein as "HGT4004").

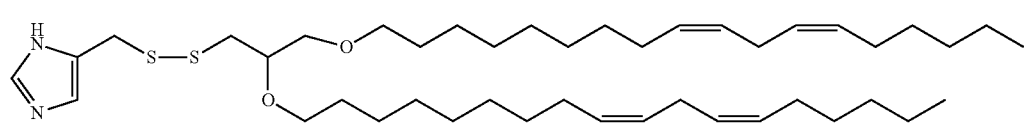

(XIV)

In still other embodiments, the cleavable lipid is the compound 1-(((2,3-bis((9Z,12Z)-octadeca-9,12-dien-1-yloxy)propyl)disulfanyl)methyl)guanidine having the structure of Formula XV (referred to herein as "HGT4005").

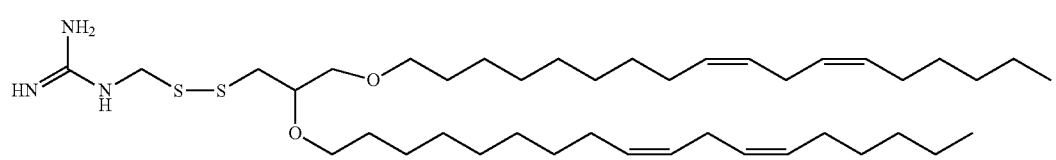

(XV)

The methods, lipids and liposomal compositions (e.g., lipid nanoparticles) described herein may be used to deliver one or more therapeutic agents to target cells, organs and tissues (e.g., hepatocytes). In certain embodiments, the contemplated therapeutic agents comprise one or more therapeutic nucleic acids or polynucleotides (e.g., DNA or RNA). Accordingly, disclosed herein are methods and compositions for modulating the expression of one or more nucleic acids in a subject. In certain embodiments, such therapeutic nucleic acids comprise or consist of RNA (e.g., mRNA, siRNA, snoRNA or microRNA).

Also disclosed herein are methods of encapsulating one or more therapeutic agents in a neutral liposomal composition. Such methods generally comprise a step of loading the liposomal composition (e.g., a lipid nanoparticle comprising the cleavable lipid HGT4002, DMG-PEG2000, cholesterol and DOPE) with the one or more therapeutic agents and contacting the liposomal composition with one or more reducing agents such that the liposomal composition is modified or neutralized. In a preferred embodiment, the liposomal composition (e.g., a lipid nanoparticle comprising one or more cleavable lipids, a PEG-modified lipid and a helper lipid) prepared in accordance with such methods are loaded with one or more therapeutic agents prior to being contacted with a reducing agent or otherwise undergoing further modification (e.g., neutralization).

In certain embodiments, the lipid compounds disclosed herein are cationic and/or ionizable lipids, that may be used as a liposomal composition or alternatively as component of a liposomal composition (e.g., a lipid nanoparticle). In certain embodiments, the compounds disclosed herein are used to enrich a liposomal composition (e.g., lipid nanoparticles), thereby conferring improved properties to such enriched liposomal composition (e.g., improved delivery of encapsulated polynucleotides to one or more target cells and/or reduced in vivo toxicity of a liposomal composition). Accordingly, also contemplated are liposomal compositions, and in particular lipid nanoparticles, that comprise one or more of the lipids disclosed herein. In certain embodiments, such liposomal compositions comprise one or more of a PEG-modified lipid, a non-cationic lipid and a helper lipid.

In certain embodiments one or more of the liposomal compositions described herein (e.g., lipid nanoparticles) comprise one or more additional lipids. For example, lipid nanoparticles that comprise or are otherwise enriched with one or more of the cleavable lipid compounds disclosed herein may further comprise one or more of DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA, DLin-KC2-DMA, C12-200 and ICE. In one embodiment the liposomal composition is a lipid nanoparticle that comprises HGT4001, DOPE and DMG-PEG2000. In another embodiment the liposomal composition is a lipid nanoparticle that comprises HGT4003, DOPE, cholesterol and DMG-PEG2000.

In certain embodiments one or more of the liposomal compositions described herein may comprise one or more PEG-modified lipids. For example, lipid nanoparticles that comprise or are otherwise enriched with one or more of the lipid compounds disclosed herein may further comprise one or more of PEG-modified lipids that comprise a poly(ethylene)glycol chain of up to 5 kDa in length covalently attached to a lipid comprising one or more $C_6$-$C_{20}$ alkyls.

Similarly, the liposomal compositions disclosed herein (e.g., lipid nanoparticles) may comprise or may otherwise be enriched with one or more of the lipid compounds disclosed herein and may further comprise one or more of helper lipids that are selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)), DOPE (1,2-dioleoyl-sn-glycero-3-phosphoethanolamine), DSPE (1,2-distearoyl-sn-glycero-3-phosphoethanolamine), DLPE (1,2-dilauroyl-sn-glycero-3-phosphoethanolamine), DPPS (1,2-dipalmitoyl-sn-glycero-3-phospho-L-serine), ceramides, sphingomyelins and cholesterol.

In certain embodiments, the cleavable lipids and the liposomal compositions comprising such lipids (e.g., lipid nanoparticles) comprise one or more polynucleotides (e.g., encapsulated DNA or RNA). In other embodiments, the one or more polynucleotides comprise at least one locked nucleic acid (e.g., two, three, four, five, six, seven, eight, nine, ten, twelve, fifteen, sixteen, eighteen, twenty, or more locked nucleic acid residues or monomers). Where the one or more encapsulated polynucleotides comprise RNA, such RNA may include, for example, mRNA, siRNA, snoRNA, microRNA, and combinations thereof.

In certain embodiments, the polynucleotides encapsulated in the pharmaceutical and liposomal compositions hereof comprise mRNA encoding, for example, a functional polypeptide, protein or enzyme, and upon being expressed (i.e., translated) by one or more target cells a functional polypeptide product (e.g., a protein or enzyme) is produced, and in some instances secreted by the target cell into the peripheral circulation of a subject. In certain embodiments, the one or more of the polynucleotides that comprise (or are otherwise loaded or encapsulated into) the compounds and pharmaceutical and liposomal compositions described herein encode a nucleic acid (e.g., a polypeptide) which is aberrantly expressed by the subject. In certain embodiments, the one or more of the encapsulated polynucleotides that comprise such compounds or liposomal compositions (e.g., a lipid nanoparticle) encode a functional protein or enzyme such as a urea cycle enzyme (e.g., ornithine transcarbamylase (OTC), carbamoyl-phosphate synthetase 1 (CPS1), argininosuccinate synthetase (ASS1), argininosuccinate lyase (ASL) or arginase 1 (ARG1)). In certain embodiments the one or more of the encapsulated polynucleotides comprises mRNA encoding an enzyme associated with a lysosomal storage disorder (e.g., the encapsulated polynucleotide is mRNA encoding one or more of the enzymes alpha galactosidase A, iduronate-2-sulfatase, iduronate sulfatase, N-acetylglucosamine-1-phosphate transferase, beta-glucosidase and galactocerebrosidase). In other embodiments where the nucleic acids comprise mRNA, such mRNA may encode one or more proteins or enzymes, for example, proteins or enzymes that may be deficient in a subject (e.g., an enzyme or protein selected from the group of enzymes consisting of erythropoietin, human growth hormone, cystic fibrosis transmembrane conductance regulator (CFTR), alpha-L-iduronidase, N-acetylglucosaminidase, alpha-glucosaminide acetyltransferase, N-acetylglucosamine 6-sulfatase, N-acetylgalactosamine-4-sulfatase, galactose-6-sulfate sulfatase, beta-galactosidase, beta-glucuronidase, glucocerebrosidase, heparan sulfamidase, heparin-N-sulfatase, lysosomal acid lipase, acid alpha-glucosidase, arylsulfatase A and hyaluronidase).

Also contemplated herein are pharmaceutical and liposomal compositions (e.g., lipid nanoparticles) that comprise one or more of the lipid compounds disclosed herein and one or more polynucleotides (e.g., antisense oligonucleotides), and in particular polynucleotides that comprises one or more chemical modifications. For example, in certain embodiments where the polynucleotide is mRNA, such chemical modifications render the mRNA more stable and may comprise, for example an end blocking modification of a 5' or 3'untranslated region of the mRNA. In certain embodiments, the chemical modification comprises the inclusion of a partial sequence of a CMV immediate-early 1 (IE1) gene to the 5' untranslated region of the mRNA. In other embodiments the chemical modification comprises the inclusion of a poly A tail to the 3' untranslated region of the mRNA. Also contemplated are chemical modifications that comprise the inclusion of a Cap1 structure to the 5' untranslated region of the mRNA. In still other embodiments, the chemical modification comprises the inclusion of a sequence encoding human growth hormone (hGH) to the 3' untranslated region of the mRNA.

The lipids and liposomal compositions described herein may be formulated to specifically target and/or transfect one or more target cells, tissues and organs. In certain embodiments, such lipids and liposomal compositions facilitate the transfection of such target cells by one or more mechanisms (e.g., fusogenic-based release and/or proton-sponge mediated disruption of the lipid-bilayer membrane of the target cells). Contemplated target cells include, for example, one or more cells selected from the group consisting of hepatocytes, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Also disclosed are methods of treating disease (e.g., a disease associated with the aberrant expression of a gene or nucleic acid) in a subject, wherein the method comprises administering one or more of the lipids and/or liposomal compositions described herein to the subject. Also contemplated are methods of transfecting one or more target cells with one or more polynucleotides, wherein the method comprises contacting the one or more target cells with the lipids or liposomal compositions described herein such that the one or more target cells are transfected with the one or more polynucleotides encapsulated therein.

The above discussed and many other features and attendant advantages of the present invention will become better understood by reference to the following detailed description of the invention when taken in conjunction with the accompanying examples. The various embodiments described herein are complimentary and can be combined or

BRIEF DESCRIPTION OF THE DRAWINGS

As illustrated in FIG. 2, the neutralized lipid nanoparticle is contacted with a functional R group that is capable of reacting with the sulfhydryl (—SH) functional groups coating the surface of the lipid nanoparticle and thereby binds the functional R group to the surface of the lipid nanoparticle by way of a newly formed disulfide bond.

DETAILED DESCRIPTION

Figure 1:
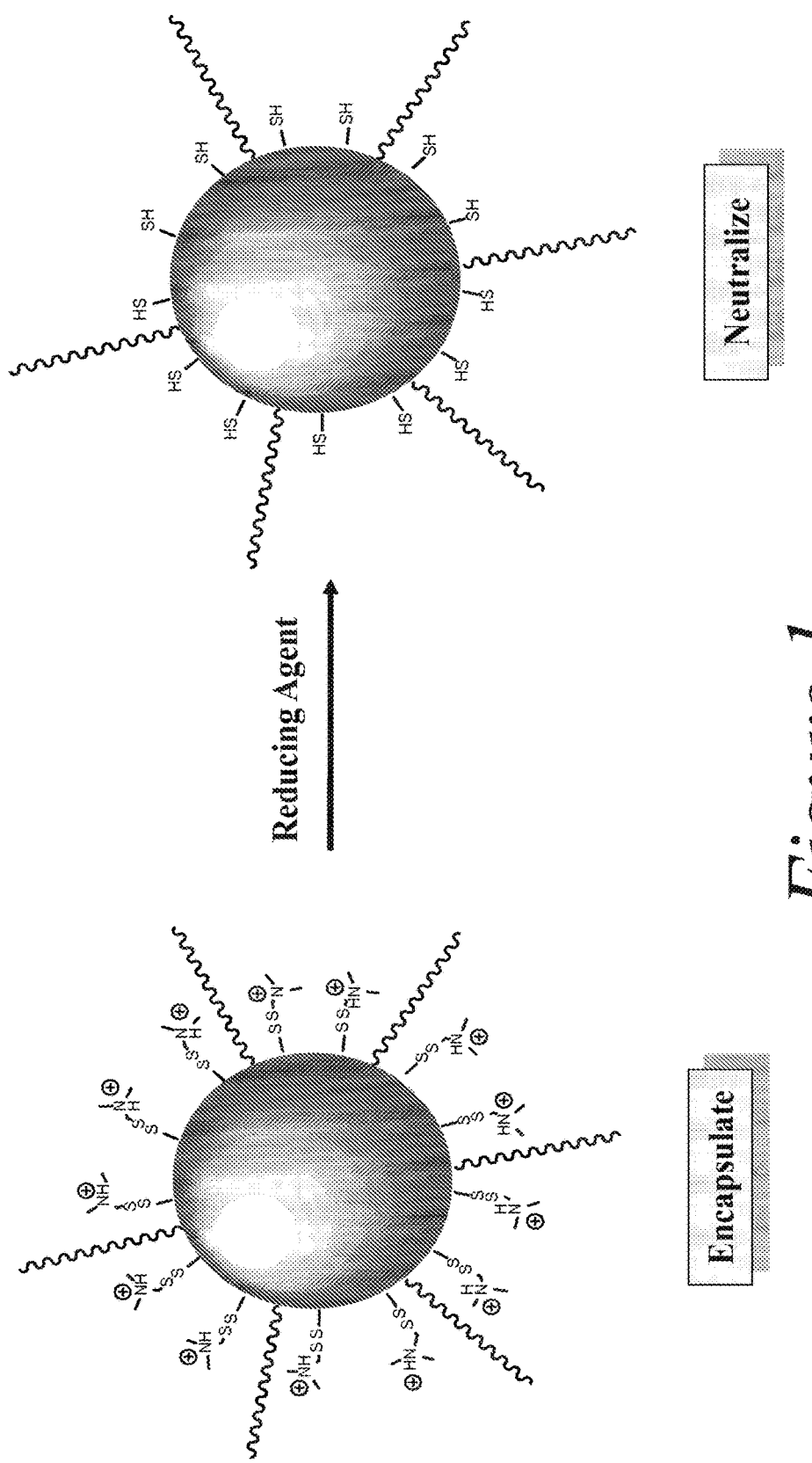
FIG. 1. illustrates one embodiment of the present invention whereby a lipid nanoparticle that comprises a cleavable disulfide (S—S) cationic lipid and which is loaded with one or more therapeutic agents is contacted with a reducing agent. As depicted in FIG. 1, prior to contacting the lipid nanoparticle with a reducing agent, the surface of the lipid nanoparticle is positively charged by the ionizable cationic head-groups of the cleavable lipid. Contacting the lipid nanoparticle with the reducing agent causes the disulfide bond (S—S) of the cationic lipid to be cleaved and the cationic amino head-group of the cleavable lipid to dissociate from the lipid nanoparticle. In the depicted embodiment, the surface of the resultant lipid nanoparticle is rendered neutralized.

Provided herein are novel lipids and liposomal compositions (e.g., lipid nanoparticles) prepared using such novel lipids. The compositions disclosed herein address many of the limitations associated with traditional surface charge neutral liposomal delivery systems, for example, the poor encapsulation efficiencies that are frequently associated with charge neural lipids. In certain instances, the inventions described herein generally relate to novel cleavable lipids (e.g., cleavable cationic lipids) and methods of using such lipids to facilitate the efficient encapsulation of one or more therapeutic agents (e.g., polynucleotides) in a liposomal composition (e.g., a lipid nanoparticle).

The pharmacokinetic properties and the ability of a systemically-administered lipid- or liposomal-based composition (e.g., a lipid nanoparticle) to reach a target cell, organ or tissue are frequently influenced by such composition's surface charge. For example, following systemic administration to a subject, liposomal compositions having a high surface charge are more likely to interact with certain cells, organs or macromolecules in the peripheral circulation, and thereby expedite the excretion of such liposomal compositions before they reach the target cells or tissues. As a result, the efficacy and utility of some liposomal-based composition and the therapeutic agents encapsulated therein may be significantly limited.

Lipid- and liposomal-based compositions (e.g., lipid nanoparticles) that are characterized as being relatively charge neural frequently have demonstrated improved pharmacokinetic characteristics relative to their charged counterparts; however, such charge neutral liposomal compositions have been traditionally plagued with poor encapsulation efficiencies, particularly with respect to the encapsulation of nucleic acids or polynucleotides. For example, neutral lipids and surface charge neutral liposomal compositions prepared from such lipids demonstrate extremely low encapsulation efficiencies, which are frequently less than 10% with respect to nucleic acid-based therapies. There remains an art-recognized need for lipid nanoparticles that carry a relatively neutral surface charge and that demonstrated high encapsulation efficiencies.

Disclosed herein are novel lipids, liposomal compositions and related methods of use that demonstrate improved encapsulation efficiencies, the surface charges of which can be neutralized or otherwise modified. The lipids and related methods described herein therefore retain beneficial properties that are generally associated with charged lipids (e.g., high encapsulation efficiencies), and in certain embodiments can be designed to carry a relatively neutral surface charge.

In general, the lipids disclosed herein comprise a hydrophilic (polar) head-group which is bound to a lipophilic (non-polar) group by way of an intermediate linker group. Such lipids may be used to prepare liposomal compositions (e.g., lipid nanoparticles) suitable for encapsulating one or more therapeutic agents (e.g., polynucleotides encoding a functional protein or enzyme). In certain embodiments, the linker group that comprises the lipids of the present invention can be cleaved, for example by exposure of the lipid to a reducing agent or environment, and the hydrophilic head-group liberated to thereby neutralize or otherwise modify the surface charge of the lipid or liposomal composition. In a preferred embodiment, the lipids of the present invention are formulated as a component of a liposomal composition and the surface charge of such composition neutralized or otherwise modified after a therapeutic agent has been encapsulated in such composition. Encapsulating the therapeutic agents within the liposomal composition while the surface of such composition is charged improves encapsulation efficiency.

In certain embodiments, the methods disclosed herein comprise a step of contacting the lipid (or the liposomal composition of which the lipid is a component) with one or more agents such that the polar head-group ($R_1$) of the lipid may be cleaved or otherwise released from one or more of the cleavable lipids that comprise the liposomal composition (e.g., by reduction of the cleavable linker group), thereby causing the lipophilic $R_2$ group to remain as a component of the lipid nanoparticle. Cleavage and/or release of the polar head-group ($R_1$) from the lipid causes the overall charge of the remaining lipid (and the liposomal composition of which the lipid is a component) to be modified, and in certain instances causes the lipid nanoparticle to be neutralized.

As used herein, the terms "neutral" and "neutralize" refer to a lipid, and in particular a liposomal composition (e.g., a lipid nanoparticle) that is substantially surface charge neutral or that is rendered substantially surface charge neutral in accordance with the methods provided herein. For example, in certain embodiments, a cationic lipid disclosed herein may be used to prepare a liposomal composition (e.g., a lipid nanoparticle) having a positive surface charge (e.g., $Z_{ave}$ of about +30 mV) and that encapsulates one or more polynucleotides. Such liposomal composition may be modified in accordance with the teachings provided herein such that the composition is rendered relatively neutralized (e.g., $Z_{ave}$ between about −3.0 mV and +3.0 mV). In certain embodiments, the neutral lipid nanoparticles described herein may be characterized as having a $Z_{ave}$ between about −10.0 mV and +10.0 mV (e.g., about +10 mV, +8 mV, +7.5 mV, +6 mV, +5 mV, +4 mV, +3 mV, +2.5 mV, +2 mV, +1 mV, +0.5 mV, +0.25 mV, 0 mV, −0.25 mV, −0.5 mV, −1 mV, −2 mV, −2.5 mV, −3 mV, −4 mV, −5 mV, −7.5 mV or −10 mV), or preferably between about −2.5 mV and +2.5 mV. Alternatively, in certain embodiments the modified lipid nanoparticles described herein may be characterized as having a $Z_{ave}$ between about −5 mV to about −50 mV.

The average zeta potential ($Z_{ave}$) is indicative of the mean surface charge of a population of liposomal compositions and represents a measure of the mean electric charge of such liposomal composition. The $Z_{ave}$ affects particle size, particle stability, encapsulation efficiency and the pharmacokinetic properties of a liposomal composition. In certain embodiments where the therapeutic agent to be encapsulated comprises an anionic polynucleotide (e.g., mRNA encoding a functional enzyme) it may be more efficient to encapsulate such polynucleotide in a liposomal compositions that incorporates one or more cationic lipids of the present invention. In such an embodiment, the interaction with and encapsulation of the anionic polynucleotide within the cationic lipid bilayer of the liposomal composition serves to enhance the encapsulation efficiency of the liposomal composition. In certain embodiments, once the therapeutic agent has been encapsulated, the surface charge of the liposomal composition may be modified (e.g., neutralized) in accordance with the teachings hereof.

In certain embodiments, the lipids disclosed herein have the structure depicted by Formula I:

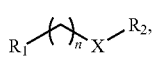
(I)

wherein $R_1$ represents the hydrophilic (polar) group and $R_2$ represents the lipophilic (non-polar) group. In certain embodiments, $R_1$ is selected from the group consisting of imidazole, guanidinium, imine, enamine, amino, an optionally-substituted alkyl amino (e.g., an alkyl amino such as dimethylamino) and an optionally-substituted pyridyl. In certain embodiments, $R_2$ is selected from the group consisting of

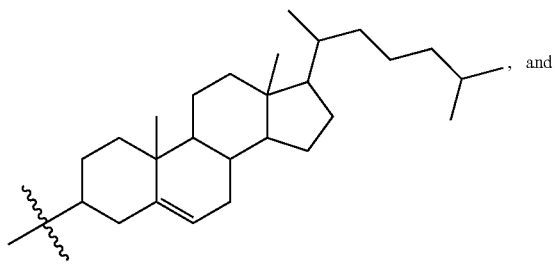
(II)
, and

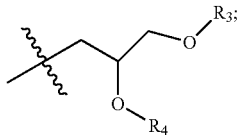
(III)

and $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl. In certain embodiments, n is zero or any positive integer (e.g., 1, 2, 3, 4, 5, 6, 7, 8, 9, 10, 11, 12, 13, 14, 15, 16, 17, 18, 19, 20 or more). The lipids disclosed herein generally comprise a cleavable linker group, represented by x in formula I.

As used herein, the term "alkyl" refers to both straight and branched chain $C_1$-$C_{40}$ hydrocarbons (e.g., $C_6$-$C_{20}$ hydrocarbons), and include both saturated and unsaturated hydrocarbons. In certain embodiments, the alkyl may comprise one or more cyclic alkyls and/or one or more heteroatoms such as oxygen, nitrogen, or sulfur and may optionally be substituted with substituents (e.g., one or more of alkyl, halo, alkoxyl, hydroxy, amino, aryl, ether, ester or amide). In certain embodiments, a contemplated alkyl includes (9Z, 12Z)-octadeca-9,12-dien. The use of designations such as, for example, "$C_6$-$C_{20}$" is intended to refer to an alkyl (e.g., straight or branched chain and inclusive of alkenes and alkyls) having the recited range carbon atoms. As used herein, the term "aryl" refers to aromatic groups (e.g., monocyclic, bicyclic and tricyclic structures) containing six to ten carbons in the ring portion. The aryl groups may be optionally substituted through available carbon atoms and in certain embodiments may include one or more heteroatoms such as oxygen, nitrogen or sulfur.

As used herein, the phrase "linker group" refers to an organic functional moiety that is covalently bound to the hydrophilic (polar) head-group and the lipophilic (non-polar) tail-group. In accordance with certain embodiments of the present inventions, the linker group can be cleaved (e.g., by hydrolysis, reduction or enzymatically) upon being contacted with one or more agents, thereby causing the dissociation of the head-group from the remaining tail-group. It should be noted that the terms "head-group" and "tail-group" as used herein to describe the lipids of the present invention, and in particular functional groups that comprise such lipids, are used for ease of reference to describe the orientation of one or more functional groups relative to other functional groups. For example, in certain embodiments a hydrophilic head-group (e.g., guanidinium) is bound (e.g., by one or more of hydrogen-bonds, van der Waals' forces, ionic interactions and covalent bonds) to a cleavable linker group (e.g., a disulfide group), which in turn is bound to a hydrophobic tail-group (e.g., cholesterol).

In certain embodiments, at least one of the functional groups or moieties that comprise the lipids disclosed herein is hydrophobic in nature (e.g., a hydrophobic tail-group comprising a naturally-occurring lipid such as cholesterol). As used herein, the term "hydrophobic" is used to indicate in qualitative terms that a functional group is water-avoiding, and typically such groups are not water soluble. For example, disclosed herein are compounds that comprise a cleavable functional group (e.g., a disulfide (S—S) group) bound to one or more hydrophobic groups, wherein such hydrophobic groups comprise one or more naturally occurring lipids such as cholesterol, and/or an optionally substituted, variably saturated or unsaturated $C_6$-$C_{20}$ alkyl and/or an optionally substituted, variably saturated or unsaturated $C_6$-$C_{20}$ acyl.

In certain embodiments, at least one of the functional groups or moieties that comprise the lipids disclosed herein is hydrophilic in nature (e.g., a hydrophilic head-group comprising a cationic imidazole moiety). As used herein, the term "hydrophilic" is used to indicate in qualitative terms that a functional group is water-preferring, and typically such groups are water-soluble. For example, disclosed herein are compounds that comprise a cleavable disulfide (S—S) functional group bound to one or more hydrophilic groups (e.g., a hydrophilic head-group), wherein such hydrophilic groups comprise or are selected from the group consisting of imidazole, guanidinium, amino, imine, enamine, an optionally-substituted alkyl amino (e.g., an alkyl amino such as dimethylamino) and pyridyl. In certain embodiments, the hydrophilic head-group of the lipid is charged (e.g., a cationic imidazole head-group). Upon cleavage of such a charged linker group from the lipid in accordance with the teachings of the present invention, the hydrophilic head-group bound thereto is liberated from the lipid and the properties of the remaining lipid (or the liposomal composition of which such remaining lipid is a component) thereby modified (e.g., neutralized).

In one embodiment, the present invention relates to a method of neutralizing or otherwise modifying a liposomal composition (e.g., a lipid nanoparticle) such that the surface charge of such composition is modified. Generally, such liposomal compositions (e.g., lipid nanoparticles) comprise at least one lipid that has a head-group (e.g., a cationic head-group) that is bound (e.g., covalently bound) to a linker group. In some embodiments, the linker group is (or comprises) a functional group that is susceptible to cleavage (e.g., chemical or enzymatic cleavage). Such cleavage may be catalyzed upon exposure to one or more agents or environments or conditions (e.g., by reduction, hydrolysis or any number of suitable mechanisms known to those of skill the art). The dissociation of the polar head-group from the lipid (e.g., as may be observed upon cleavage of the linker group) results in a modification of the charge of such lipid (or the liposomal composition of which such lipid is a component). In certain embodiments, the linker group comprises an ester functional group.

In certain embodiments, the lipid compounds disclosed herein generally comprise one or more cleavable linker groups. For example, such linker groups may comprise or consist of one or more disulfide (S—S) functional groups as depicted in Formula IV below:

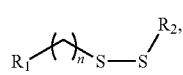 (IV)

wherein $R_1$ represents a hydrophilic (polar) head-group and $R_2$ represents a lipophilic (non-polar) tail-group. In certain embodiments, $R_1$ may be selected from the group consisting of imidazole, guanidinium, imine, enamine, amino, an optionally-substituted alkyl amino (e.g., an alkyl amino such as dimethylamino) and an optionally-substituted pyridyl. In certain embodiments, $R_2$ may be selected from the group consisting of:

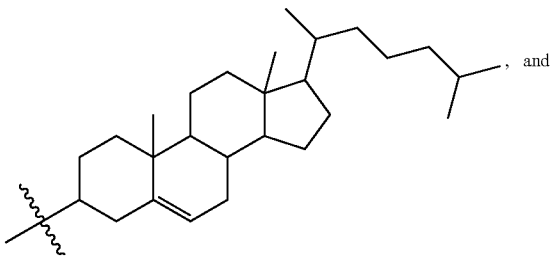

wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl. In certain embodiments, n is 1 (such that the alkyl is ethyl), 2 (such that the alkyl is methyl), 3 (such that the alkyl is, for example, propyl or iso-propyl), 4 (such that the alkyl is, for example, butyl, iso-butyl, sec-butyl or ter-butyl), 5 (such that the alkyl is, for example, pentane), 6 (such that the alkyl is, for example, hexane), 7 (such that the alkyl is, for example, heptane), 8 (such that the alkyl is, for example, octane), 9 (n such that the alkyl is, for example, nonane) or 10 (such that the alkyl is, for example, decane).

As used herein to refer to a lipid or a linker group, the terms "cleave" and "cleavable" generally mean that one or more chemical bonds (e.g., one or more of covalent bonds, hydrogen-bonds, van der Waals' forces and/or ionic interactions) between atoms in or adjacent to the subject functional group (e.g., a disulfide linker group) are broken (e.g., hydrolyzed, reduced or oxidized) or are capable of being broken upon exposure to a selected agent or condition. For example, an acid-labile linker group may be cleavable upon exposure to acidic conditions (e.g., pH less than about 7.0). In certain embodiments, the cleavable group is a disulfide functional group, and in particular embodiments is a disulfide group that is capable of being cleaved upon exposure to selected biological conditions (e.g., intracellular conditions). In certain embodiments, the cleavable group is an ester functional group that is capable of being cleaved upon exposure to selected biological conditions. For example, a disulfide function groups may be cleaved enzymatically or by a hydrolysis, or alternatively upon exposure to reducing conditions. Upon cleavage of such disulfide functional group, the one or more functional moieties or groups (e.g., a head-group) that are bound thereto may be liberated. Exemplary cleavable groups may include, but are not limited to, disulfide groups, ester groups, ether groups, and any derivatives thereof (e.g., alkyl and aryl esters). In certain embodiments, the cleavable group is not an ester group or an ether group.

Enzyme-cleavable groups have been employed for many drug delivery systems and a large portion of such systems have been in the context of a prodrug. (Sherwood, R. F. *Adv. Drug Del. Rev.* 1996, 22, 269-288). In certain embodiments, such enzymes may also be employed to cleave one or more functional groups of the compositions disclosed herein. Exemplary enzymes utilized within the context of prodrugs and that may also be employed to cleave one or more functional groups may include, but not be limited to, alkaline phosphatase, carboxypeptidase G2, cytosine deaminase, nitroreductase, β-glucuronidase, α-galactosidase, thioredoxin and gamma-interferon inducible lysosomal thiol reductase (GILT). Further, many enzyme-cleavable groups are related to the specific recognition of a peptide sequence. Exemplary enzyme-cleavable sequences contemplated by the present invention (and their corresponding enzyme) include, but are not limited to, Val-Cit dipeptide (Cathepsin B) (Toki, et al. J. Org. Chem. 2002, 67: 1866-1872; Yoneda, et al. Bioorg. Med. Chem. Lett. 2008, 18: 1632-1636), GFLG (Cathepsin B) (Nori, et al. Bioconj. Chem. 2003, 14: 44-50; Veronese, et al. Bioconj. Chem, 2005, 16: 775-784), GGGF (Cathepsin B) (DeNardo, et al. Clin. Canc. Res. 2003, 9: 3665s-3972s), PVGLIG (MMP) (Chau, et al. J. Pharm. Sci. 2006, 95: 542-551), AAN (legumain) (Stern et al. Bioconj. Chem. 2009, 20: 500-510).

In certain embodiments, the cleavable group may be an acid-labile functional groups. For example, acid-labile functional groups employed for enhanced drug release from a host of drug delivery systems such as prodrug conjugates, polymer conjugates, nanoparticles and lipid-based systems may be employed in the compositions and methods disclosed herein. Contemplated acid-labile functional groups or linkages may include, for example, a hydrazone moiety, an imine linkage, acetal moieties, ketal moieties, cis-aconityl systems, ortho esters, thiopropionate, maleic anhydrides, enamines and vinyl ethers.

In certain embodiments, the cleavable group may be employed to liberate one or more agents from the compositions disclosed herein. For example, contemplated is the employment of one or more agents or cargo (e.g., small molecules, proteins or nucleic acids) upon cleavage of, for example a disulfide functional group.

The cleavable groups described herein are generally bound (e.g., bound by one or more of hydrogen-bonds, van der Waals' forces, ionic interactions and covalent bonds) to one or more functional moieties or groups (e.g., at least one head-group and at least one tail-group). In certain embodiments, at least one of the functional moieties or groups is hydrophilic (e.g., a hydrophilic head-group comprising one or more of imidazole, guanidinium, amino, imine, enamine, optionally-substituted alkyl amino and pyridyl). In certain embodiments where there lipid compositions of the present invention are incorporated in a liposomal composition (e.g., a lipid nanoparticle), cleavage of the linker group causes the hydrophilic head-group to dissociate from the lipid while the lipophilic tail group remains as a fixed component of the liposomal composition. For example, as illustrated in FIG. 1 upon contacting a cleavable disulfide (S—S) cationic lipid with a reducing agent, the disulfide bond (S—S) is cleaved and the cationic amino head-group of the cleavable lipid dissociates from the lipid nanoparticle, while the lipophilic tail-group remains as a component of the liposomal vehicle. In the depicted embodiment, the surface of the resultant lipid nanoparticle is rendered neutralized as a result of the cleavage of the disulfide linker group.

The present inventions contemplate cleavage of the linker group by contacting such linker group with one or more suitable agents. As used herein, the term "agent" is meant to refer to one or more reagents, compounds or conditions with which (or to which) the lipids of the present invention may be contacted and/or interact to catalyze or otherwise induce cleavage of one or more linker groups. In certain embodiments, the agent is a reducing agent that is capable of donating electrons in an oxidation-reduction reaction. Contemplated agents include reducing agents, for example, aqueous solutions comprising one or more of tris (2-carboxyethyl)phosphine (TCEP), β-mercaptoethanol (β-ME), dithiothreitol (DTT), glutathione and dithioerythritol. Alternatively, in other embodiments the agent may be an oxidizing agent that is capable of accepting electrons in an oxidation-reduction reaction. In other embodiments, the agent may comprise one or more enzymes that are capable of enzymatically cleaving a linker group. Preferably, the selection of a suitable agent (e.g., a reducing agent) is based on the nature of the cleavable linker group that comprises the lipid and is within the purview of one skilled in the art. For example, a lipid comprising a linker group that is susceptible to enzymatic digestion may be contacted with or otherwise exposed to an appropriate enzyme to facilitate cleavage of the linker group and the liberation of the polar head-group from the lipid. Alternatively, in other embodiments the cleavable linker group may comprise an ester functional group, and the corresponding agent may comprise a compound or agent capable of readily hydrolyzing such ester functional group. Still in other embodiments, the cleavable linker group may comprise an acid-labile group that may be cleaved upon exposure to acidic conditions.

In certain embodiments, a linker group may be cleavable in vitro upon contacting the lipid with an appropriate agent (e.g., an aqueous solution comprising the reducing agent β-mercaptoethanol (β-ME)). For example, a lipid nanoparticle comprising one or more of the cleavable lipids of the present invention may be contacted with a reducing agent promptly after loading with one or more therapeutic agents (e.g., polynucleotides encoding a functional protein or enzyme) and thereby neutralize the lipid nanoparticle. Alternatively, a lipid nanoparticle comprising one or more cleavable lipids may be contacted with a reducing agent immediately prior to administration to a subject. Lipid nanoparticles that carry a high surface charge (e.g., $Z_{ave}$ more than about +30 mV or less than about −30 mV) are often considered more stable because the particle surface charges serve to repel similarly charged particles, thereby reducing the likelihood that similarly charged particles will aggregate together. By delaying the neutralization of the lipid nanoparticle, such that surface neutralization occurs immediately prior to administration of the lipid nanoparticle to a subject (e.g., within less than six weeks, four weeks, three weeks, two weeks, one week, or less than seventy-two hours, forty-eight hours, twenty-four hours, eighteen hours, twelve hours, nine hours, six hours, three hours, two hours, one hour, thirty minutes, fifteen minutes, ten minutes, five minutes, one minute or less), the stability of lipid nanoparticles may be preserved or otherwise or extended. Similarly, in certain embodiments, cleavage of the linker groups may be induced in vivo, for example upon exposure to circulating enzymes or conditions present in the systemic circulation, and thereby cause the surface charge of the lipid composition to be modified or neutralized. For example, a lipid nanoparticle prepared using one or more of the lipids disclosed herein (e.g., the cationic lipid HGT4002) may be prepared and loaded with an effective amount of a therapeutic agent and administered to a subject with a positive surface charge, and which becomes neutralized in vivo following administration to the subject (e.g., by enzymatic cleavage of susceptible linker groups). It should be noted that in certain embodiments, the degree to which the properties (e.g., surface charge) of a liposomal composition (e.g., a lipid nanoparticle) are modified is a function of the selected reducing agents to which the liposomal composition is exposed and/or the duration of such exposure.

While in some embodiments described herein, the terms "modified" and "modulated", as they relate to the surface charge of a liposomal composition, refer to the neutralization of a liposomal composition (e.g., modulating the $Z_{ave}$ such that it is between about −2.5 mV and +2.5 mV), the present inventions need not be limited to neutralization. Rather, the terms "modified" and "modulated" when used with respect to the surface charge of a liposomal composition are intended to refer broadly to any changes in the physical or chemical properties of such liposomal composition (e.g., modulating a net positive surface charge of a liposomal composition such that the net surface charge is negative). The selected agent and the duration of exposure of the liposomal composition to such agent represent two important variables that can be manipulated by one of skill in the art such that the surface charge of the liposomal composition may be modified or modulated to a desired degree (e.g., $Z_{ave}$ less than about −5 mV). Accordingly, in certain embodiments, the lipid nanoparticle is contacted with a selected reducing agent for a selected duration sufficient to achieve the desired result (e.g., reduction in the surface charge by at least about 1-99%). In certain embodiments, a liposomal composition may be contacted with a selected agent for between about five minutes to about seventy-two hours or more (e.g., at least about fifteen minutes, thirty minutes, forty-five minutes, one hour, three hours, six hours, eight hours, twelve hours, sixteen hours, eighteen hours, twenty four hours, forty-eight hours, seventy-two hours, or longer) to achieve one or more desired outcomes or results.

In certain embodiments, there exists a direct relationship between the duration of exposure of the liposomal composition to the selected agent and the resulting change in the surface charge of the liposomal composition. For example, by extending the duration of exposure of a lipid nanoparticle having a net positive surface charge to one or more agents (e.g., a reducing agent) the resulting surface charge of such lipid nanoparticle may be neutralized or reduced to a greater degree (e.g., reducing the average zeta potential to less than about −0.5 mV, −1.0 mV, −2.5 mV, −5.0 mV, −7.0 mV, −10.0 mV, −12.5 mV, −15.0 mV, −17.5 mV, −20 mV, −25 mV, −30 mV, −40 mV, −50 mV, or less). In some embodiments, the degree to which the net surface charge of a liposomal composition may be modulated by the methods disclosed herein may also be a function of the properties of the lipid components that comprise such liposomal composition (e.g., one or more helper lipids or PEG-derivatized lipids). Accordingly, the present invention provides means of controlling the surface charge of liposomal compositions (and in particular liposomal compositions encapsulating one or more therapeutic agents) based on, for example, one or more desired physical properties or targeted organs or tissues. The foregoing is particularly useful for not only facilitating the targeting of liposomal compositions to specific cells, tissues or organs, but in certain embodiments may serve to mitigate toxicities associated with some liposomal compositions, and in particular cationic liposomal compositions. For example, in some embodiments reducing the surface charge of the liposomal compositions disclosed herein reduces the toxicities associated with such liposomal compositions by minimizing immunogenicity or by minimizing events associated with complement activation.

Upon contacting the lipid with one or more agents (e.g., an aqueous solution comprising at least one agent), the linker group is cleaved from the lipid and a hydrophilic head-group liberated, leaving the lipophilic (non-polar) tail-group as a component of the liposomal composition (e.g., a lipid nanoparticle). In embodiments where the cleavable lipid comprises a disulfide (S—S) linker group, upon exposure to a reducing agent (e.g., an aqueous solution of tris (2-carboxyethyl)phosphine (TCEP) and/or β-mercaptoethanol (β-ME)), the hydrophilic head-group represented by the following structure is liberated:

(V)

wherein $R_1$ represents the hydrophilic head-group (e.g., imidazole, guanidinium, imine, enamine, amino, an optionally-substituted alkyl amino, and pyridyl). Similarly, following exposure of the lipid, and in particular a cleavable disulfide linker group that comprises the lipid, to one or more reducing agents, a thiol group, as represented by the following structure, remains as a fixed component of the liposomal composition (e.g., lipid nanoparticle):

(VI)

wherein $R_2$ represents the tail-group and is selected from the group consisting of an optionally-substituted pyridyl (e.g., pyridine or nitropyridyl) or one of the following structures:

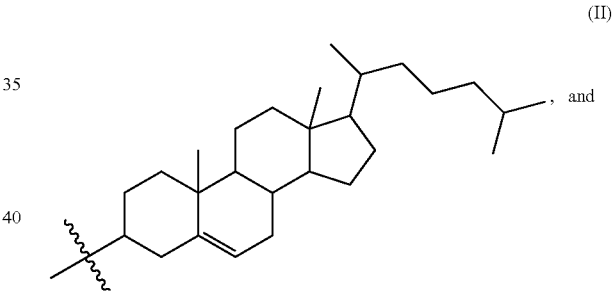

(II)

, and

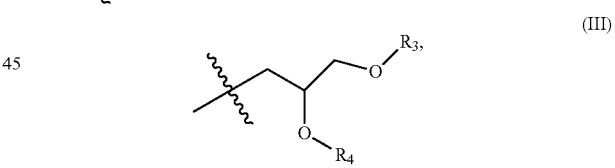

Figure 2:
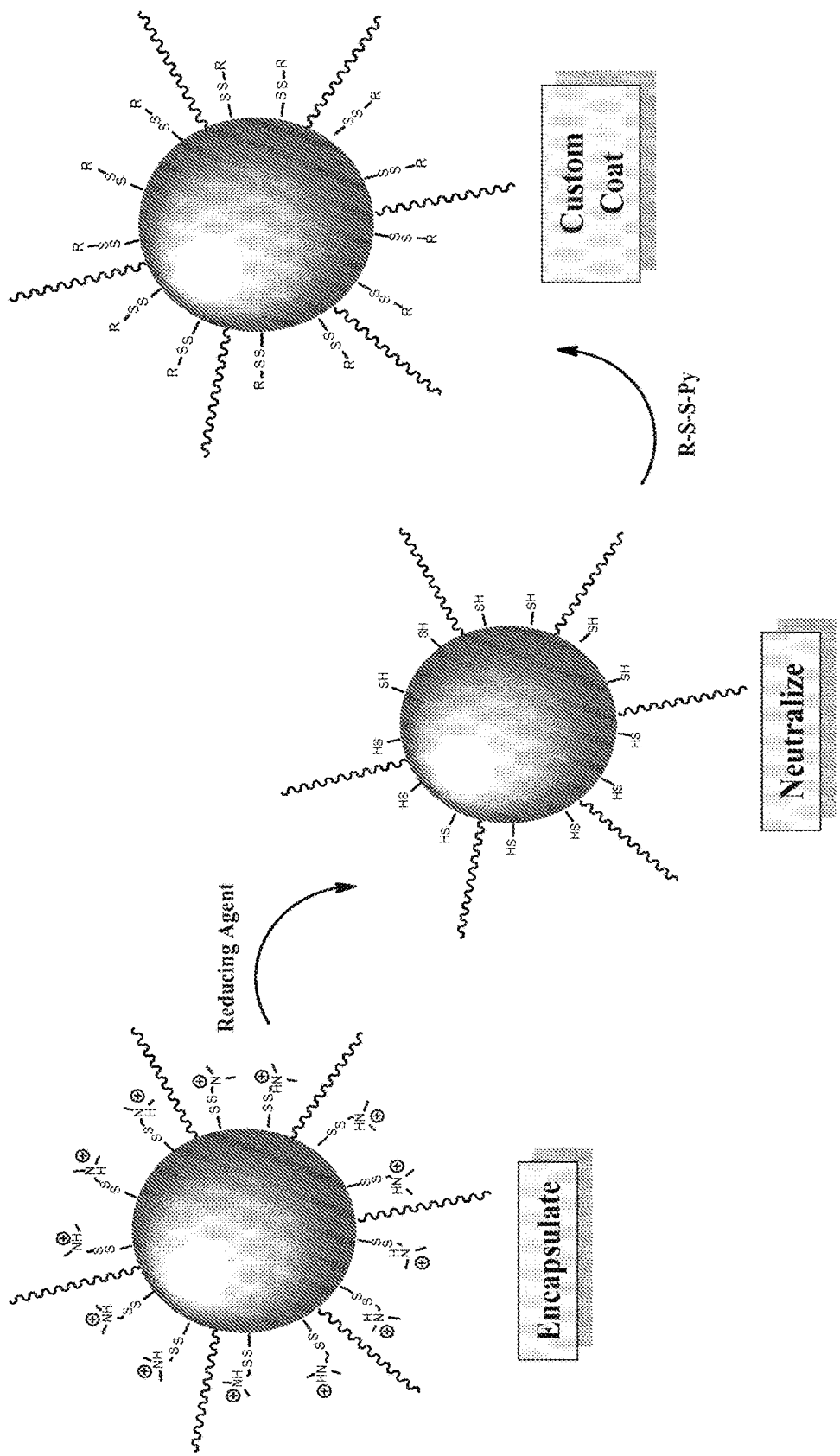
FIG. 2. illustrates one embodiment of the present invention whereby a lipid nanoparticle that comprises a cleavable disulfide (S—S) cationic lipid and which is loaded with one or more therapeutic agents is neutralized by contacting it with a reducing agent. The neutralized lipid is further modified to introduce different functional groups or chemistries. As depicted in FIG. 2, prior to contacting the lipid nanoparticle with a reducing agent, the surface of the lipid nanoparticle is positively charged by the ionizable cationic head-groups of the cleavable lipid. Contacting the lipid nanoparticle with the reducing agent causes the disulfide bond (S—S) of the cationic lipid to be cleaved and the cationic amino head-groups of the cleavable lipid to dissociate from the lipid nanoparticle. The surface of the resultant lipid nanoparticle is rendered neutralized, and as illustrated is coated with sulfhydryl (—SH) functional groups, which may be further reacted to introduce additional functional groups or chemistries.

(III)

wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl, remains as a component of the liposomal composition (e.g., lipid nanoparticle). As depicted in FIG. 2, following exposure of the liposomal composition to a reducing agent, the remaining thiol functional groups that coat the surface of the modified or neutralized composition may be further manipulated. In the embodiment depicted in FIG. 2, the thiol groups represent substrates that may be reacted with other organic compounds, polymers, peptides or ligands to further modify the surface of the liposomal composition.

Accordingly, also disclosed herein are compositions and methods of further modifying the lipids and the liposomal compositions of the present invention to introduce additional functional groups or chemistries. Therefore, in certain embodiments, the term "modified" as used to characterize a lipid that has been neutralized may also refer to the further modification or customization of such neutral lipid. In such embodiments, the term "modified" may be used to characterize a modified lipid relative to the neutral lipid from which that modified lipid was prepared. For example, in certain embodiments, the foregoing contemplates the modification of the lipids disclosed herein such that a first polar head-group is removed from the lipid (e.g., upon cleavage of a linker group to thereby produce a neutralized lipid) and subsequently replaced with a second functional group of interest to thereby yield a modified lipid. The modification of the lipids to introduce additional functional groups and/or to impart additional functionalities may be used as a means of further targeting the lipid nanoparticles to tissues of interest. Therefore, also provided herein are additional means of further modifying the physical and chemical properties of one or more lipids that have been previously modified or neutralized in accordance with the present inventions. For example, in certain embodiments, the sulfhydryl group that comprises the remaining thiol group of a lipid that has been reductively neutralized in accordance with the teachings hereof, may be further reacted with one or more additional functional groups or compounds to further modify the physical and/or chemical properties of the lipid and/or the liposomal composition of which such lipid is a component. As depicted in FIG. 2, after having neutralized or modified the surface charge of the liposomal composition, the remaining sulfhydryl groups coating the external surface of the modified or neutralized lipid may be further reacted to introduce additional chemistries or functional groups. For example, the remaining thiol group of the modified or neutral lipid may be contacted or otherwise reacted with a secondary agent, structure or compound represented by the following structure:

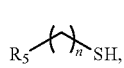
(VII)

wherein $R_5$ represents a second functional group or chemistry, and wherein n is zero or a positive integer. In certain embodiments, the second functional group is a targeting ligand that may be used to mediate the distribution of the lipid nanoparticle to target cells, tissues or organs or to encourage localization of such lipid nanoparticle at certain target cells or target tissues.

Recognition of the targeting ligand by the target tissues actively facilitates tissue distribution to, and cellular uptake of the lipid nanoparticles and/or their contents by the target cells and tissues. For example, in certain embodiments, the liposomal compositions (e.g., lipid nanoparticles) may undergo secondary modification such that a targeting ligand comprising an apolipoprotein-E targeting ligand is bound to the surface of such composition to facilitate or encourage recognition and binding of such composition to endogenous low density lipoprotein receptors expressed, for example by hepatocytes. As provided herein, the composition can comprise a targeting ligand capable of enhancing affinity of the compositions to one or more target cells. Suitable targeting ligands are selected such that the unique characteristics of a target cell are exploited, thus allowing the liposomal composition to discriminate between target and non-target cells. For example, compositions of the present invention may bear surface markers (e.g., apolipoprotein-B or apolipoprotein-E) that selectively enhance recognition of, or affinity to hepatocytes (e.g., by receptor-mediated recognition of and binding to such surface markers). Additionally, the use of galactose as a targeting ligand would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting ligands that have been conjugated to the surface of the liposomal compositions of the present invention therefore facilitate the recognition and uptake of such liposomal compositions by one or more target cells and tissues. Examples of suitable targeting ligands include one or more peptides, proteins, aptamers, vitamins and oligonucleotides.

In certain embodiments, the reduced lipid is contacted with the secondary agent, compound or functional group under conditions that facilitate the formation of a disulfide bond (e.g., oxidative conditions) and the neutral lipid thereby further modified. The further modified lipid may be represented by the following structure:

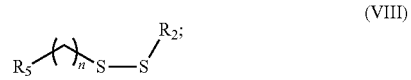
(VIII)

wherein $R_5$ represents the newly introduced second functional group or chemistry, $R_2$ represents a lipophilic tail-group and n is zero or a positive integer. The newly introduced second functional group ($R_5$) may be selected from the group consisting of a polymer (e.g., polyethylene glycol), a peptide, a targeting ligand (e.g., apolipoprotein-B, apolipoprotein-E, glucose, galactose and/or mannose), an alkyl (e.g., an optionally substituted, variably saturated or unsaturated $C_1$-$C_{20}$ alkyl) and a capping structure. In certain embodiments, the lipophilic tail-group ($R_2$) is selected from the group consisting of an optionally-substituted pyridyl (e.g., pyridine or nitropyridyl) or one of the following structures:

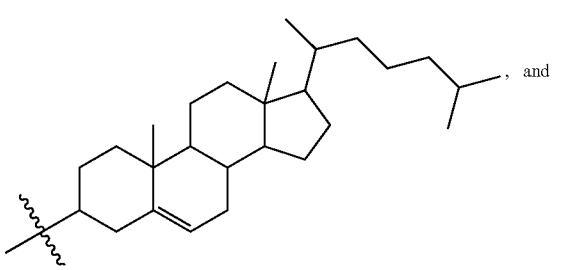
(II)
, and

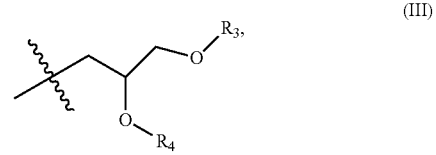
(III)

wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl. The foregoing therefore provides methods of using, for example, cleavable disulfide cationic lipids, to create a neutral thiol coated nanoparticle. Such thiol functional groups may then act as a substrate which could be used as is, or further modified with other moieties (polymers (PEG), targeting agents or capping structures).

For example, in certain embodiments, the modified lipid may be represented by one of the following structures:

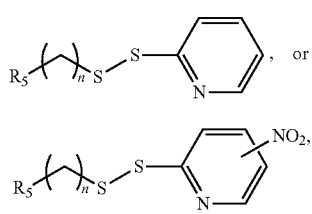

wherein $R_5$ is selected from the group consisting of a polymer (e.g., polyethylene glycol), a peptide, a targeting ligand (e.g., apolipoprotein-B, apolipoprotein-E, glucose, galactose and/or mannose), an alkyl (e.g., an optionally substituted, variably saturated or unsaturated $C_1$-$C_{20}$ alkyl) and a capping structure and wherein n is zero or any positive integer. In other embodiments, the thiol group of a modified or neutral lipid may be contacted or otherwise reacted under suitable conditions (e.g., oxidative conditions) with a secondary agent, structure or compound represented by one or more of the structures (IX) and/or (X) depicted above.

The methods disclosed herein provide means of preparing neutral or slightly charged lipids that demonstrate high encapsulation efficiency. As used herein, the phrase "encapsulation efficiency" refers to the fraction of therapeutic agent that is effectively encapsulated within a liposomal-based vehicle relative to the initial fraction of therapeutic agent present in the lipid phase. In certain embodiments, the high encapsulations efficiencies are achieved upon loading the liposomal composition (e.g., lipid nanoparticles demonstrating a positive surface charge) prior to contacting such composition with an agent (e.g., a reducing agent). By loading the liposomal vehicle in its charged state, the encapsulation of oppositely charged therapeutic agents is facilitated. Accordingly, in a preferred embodiment, the lipid compounds and liposomal vehicles prepared therefrom are loaded with one or more therapeutic agents prior to being contacted with an agent (e.g., a reducing agent). In certain embodiments, the lipid compositions and the lipid nanoparticles prepared therefrom exhibit an encapsulation efficiency of at least 50% (e.g., 55%, 60%, 65%, 70%, 75%, 80%, 85%, 87.5%, 90%, 92.5%, 95%, 97.5%, 98%, 99% or more.)

The liposomal compositions prepared in accordance with the methods disclosed herein may be characterized with respect to the average concentration of one or more therapeutic agents encapsulated in such compositions. For example, in certain embodiments, the average concentration of therapeutic agent encapsulated in a liposomal composition prepared in accordance with the present inventions is between about 0.025 µg/mL to about 250 µg/mL (e.g., at least about 0.05 µg/mL, 0.1 µg/mL, 0.25 µg/mL, 0.5 µg/mL, 1 µg/mL, 2.5 µg/mL, 5 µg/mL, 10 µg/mL, 15 µg/mL, 20 µg/mL, 25 µg/mL, 50 µg/mL, 75 µg/mL, 100 µg/mL, 150 µg/mL, 200 µg/mL, or more).

In certain embodiments the lipids and the liposomal compositions prepared using such lipids are stable. As used herein to characterize a liposomal composition, the term "stable" refers to the physical stability of such compositions and generally means that the composition is suitable for administration to a subject at the conclusion of a predetermined period of time and/or storage conditions (e.g., following storage at standard room temperature and humidity for at least two years). In certain embodiments the substantial absence of a precipitate, cloudiness and/or other particulate matter (e.g., following storage at 45° C. for at least two months) in the composition may be indicative of its stability. In other embodiments, the substantial absence of particle aggregation or coalescence may be indicative of the stability of the liposomal compositions disclosed herein.

In certain embodiments, the lipid compounds, and in particular the imidazole-based compounds described herein (e.g., HGT4001 and HGT4004), are also characterized by their reduced toxicity, in particular relative to traditional cationic lipids. In some embodiments, the pharmaceutical and liposomal compositions described herein comprise one or more imidazole-based cationic lipid compounds such that the relative concentration of other more toxic cationic lipids in such pharmaceutical or liposomal composition may be reduced or otherwise eliminated. The imidazole-based compounds or lipids (e.g., HGT4001 and/or HGT4004) may be used as the sole cationic lipid in one or more of the pharmaceutical and liposomal compositions described herein (e.g., lipid nanoparticles), or alternatively may be combined with traditional cationic lipids (e.g., LIPOFECTIN or LIPOFECTAMINE), non-cationic lipids, PEG-modified lipids and/or helper lipids. In certain embodiments, the liposomal compositions (e.g., lipid nanoparticles) may comprise a molar ratio of about 1% to about 90%, about 2% to about 70%, about 5% to about 50%, about 10% to about 40% of the total lipid present in such pharmaceutical or liposomal composition (e.g., a lipid nanoparticle), or preferably about 20% to about 70% of the total lipid present in such pharmaceutical or liposomal composition (e.g., a lipid nanoparticle).

The cleavable lipids described herein, and in particular, the disulfide cleavable lipid may consist of one or more of the lipid compounds disclosed in co-owned U.S. Application No. 61/494,745 the contents of which are incorporated herein by reference in their entirety. For example, in certain embodiments, the inventions relate to the compound 5-(((10, 13-dimethyl-17-(6-methylheptan-2-yl)-2,3,4,7,8,9,10,11,12, 13,14,15,16,17-tetradecahydro-1H-cyclopenta[a]phenanthren-3-yl)disulfanyl)methyl)-1H-imidazole, having the structure of formula XI (referred to herein as "HGT4001").

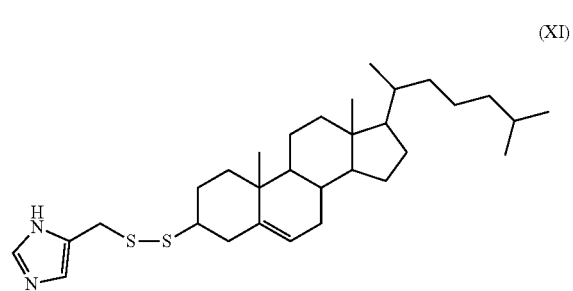 [SMILES: CC(C)CCCC(C)C1CCC2C3CC=C4CC(SSCc5cnc[nH]5)CCC4(C)C3CCC12C]

In certain embodiments, the inventions relate to the compound 1-(2-(((3S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)disulfanyl)ethyl)guanidine, having the structure of formula XII (referred to herein as "HGT4002").

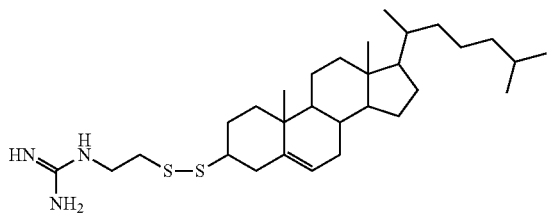
(XII)

In yet other embodiments, the inventions relate to the compound 2-((2,3-Bis((9Z,12Z)-octadeca-9,12-dien-1-yloxy)propyl)disulfanyl)-N,N-dimethylethanamine, having the structure of formula XIII (referred to herein as "HGT4003").

described herein are characterized as having one or more properties that afford such compounds advantages relative to other similarly classified lipids. For example, in certain embodiments, the lipids disclosed herein allow for the control and tailoring of the physical properties of liposomal compositions of which they are a component. In particular, the surface charge of liposomal compositions comprising the lipid compounds disclosed herein may be readily customized based on the teachings provided herein. For example, the surface charge of the liposomal composition may be rendered neutral upon exposure to an appropriate agent (e.g., a reducing agent such as TCEP). Such modification may be employed as a means of modulating the pharmacokinetic properties of a liposomal composition (e.g., by enhancing circulatory half-life or by facilitating the distribution of such composition to one or more target cells, organs or tissues). In certain embodiments the lipid compounds and the neutralized or modified liposomal compositions disclosed herein exhibit an enhanced (e.g., increased) ability to transfect one or more target cells. As used herein, the terms "transfect" or "transfection" refer to the intracellular introduction of one or more encapsulated materials (e.g., nucleic acids and/or polynucleotides) into a cell, or preferably into a target cell.

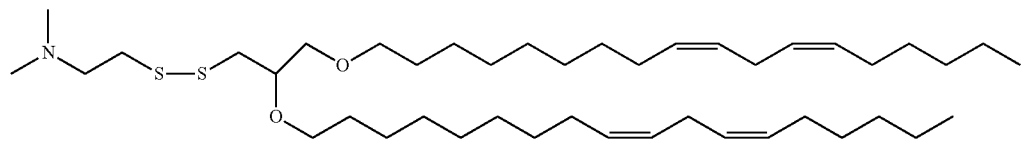
(XIII)

In other embodiments, the inventions relate to the compound 5-(((2,3-bis((9Z,12Z)-octadeca-9,12-dien-1-yloxy)propyl)disulfanyl)methyl)-1H-imidazole having the structure of formula XIV (referred to herein as "HGT4004").

The methods, lipids and liposomal compositions of the present invention may be used to facilitate the delivery of a wide range of materials and therapeutic agents to target cells, organs and tissues. Accordingly, the lipids and lipo-

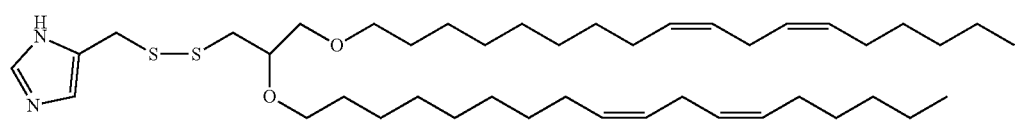
(XIV)

In still other embodiments, the inventions relate to the compound 1-(((2,3-bis((9Z,12Z)-octadeca-9,12-dien-1-yloxy)propyl)disulfanyl)methyl)guanidine having the structure of formula XV (referred to herein as "HGT4005").

somal compositions described herein may be used to encapsulate any number of materials suitable for intracellular delivery. In certain embodiments, such encapsulated materials are capable of conferring a therapeutic or diagnostic

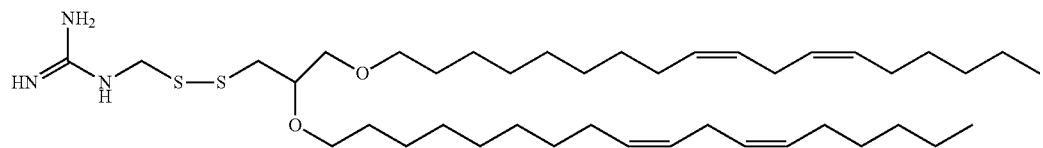
(XV)

The lipid compounds described herein may be used to construct liposomal compositions that facilitate or enhance the delivery and release of encapsulated materials (e.g., one or more therapeutic polynucleotides) to one or more target cells (e.g., by permeating or fusing with the lipid membranes of such target cells). In certain embodiments the compounds benefit upon the cells into which such materials are delivered, and may include any drugs, biologics and/or diagnostics. The materials can be organic or inorganic. Organic molecules can be peptides, proteins, carbohydrates, lipids, sterols, nucleic acids (including peptide nucleic acids), or any combination thereof. In certain embodiments, the pharmaceutical and liposomal compositions described herein can comprise or otherwise encapsulate more than one type of material, for example, two or more different polynucleotide sequences encoding a protein, an enzyme and/or a steroid. In certain embodiments, the encapsulated materials are one or more polynucleotides and nucleic acids.

As used herein, the terms "polynucleotide" and "nucleic acid" are used interchangeably to refer to genetic material (e.g., DNA or RNA), and when such terms are used with respect to the lipid compounds and liposomal compositions described herein (e.g., lipid nanoparticles) generally refer to the genetic material encapsulated by such compounds and compositions (e.g., lipid nanoparticles). In some embodiments, the polynucleotide is RNA. Suitable RNA includes mRNA, siRNA, miRNA, snRNA and snoRNA. Contemplated polynucleotides also include large intergenic non-coding RNA (lincRNA), which generally does not encode proteins, but rather function, for example, in immune signaling, stem cell biology and the development of disease. (See, e.g., Guttman, et al., 458: 223-227 (2009); and Ng, et al., Nature Genetics 42: 1035-1036 (2010), the contents of which are incorporated herein by reference). In certain embodiments, the polynucleotides encapsulated by the lipid compounds or liposomal compositions of the invention include RNA or stabilized RNA encoding a protein or enzyme (e.g., mRNA encoding alpha galactosidase A or a low density lipoprotein receptors). The present invention contemplates the use of such polynucleotides (and in particular RNA or stabilized RNA) as a therapeutic that is capable of being expressed by target cells to thereby facilitate the production (and in certain instances the excretion) of a functional enzyme or protein by such target cells as disclosed for example, in International Application No. PCT/US2010/058457 and in U.S. Provisional Application No. 61/494,881, filed Jun. 8, 2011, the teachings of which are both incorporated herein by reference in their entirety. For example, in certain embodiments, upon the expression of one or more polynucleotides by target cells the production of a functional or biologically-active enzyme or protein in which a subject is deficient (e.g., a urea cycle enzyme or an enzyme associated with a lysosomal storage disorder) may be observed.

Also contemplated by the present inventions are the modifications of polynucleotides or nucleic acids. As used herein to describe one or more polynucleotides or nucleic acids described herein (e.g., mRNA), the terms "modification" and "modified", as such terms relate to the polynucleotides or nucleic acids disclosed herein, refer to one or more changes, alterations or substitutions which improve or enhance the stability and/or expression (e.g., translation) of such polynucleotides or nucleic acids (e.g., mRNA), including for example, the inclusion of sequences which function in the initiation of protein translation (e.g., the Kozac consensus sequence). (Kozak, M., Nucleic Acids Res 15 (20): 8125-48 (1987)). In some embodiments, the nucleic acids of the present invention have undergone a chemical or biological modification to render them more stable. Exemplary modifications to a nucleic acid include the depletion of a base (e.g., by deletion or by the substitution of one nucleotide for another) or modification of a base, for example, the chemical modification of a base. The phrase "chemical modifications" as used herein to describe the nucleic acids or polynucleotides of the present invention, refers to modifications which introduce chemistries which differ from those seen in naturally occurring nucleic acids, for example, covalent modifications such as the introduction of modified nucleotides, (e.g., nucleotide analogs, or the inclusion of pendant groups which are not naturally found in such nucleic acid molecules). For example, in certain embodiments the polynucleotides disclosed herein (e.g., an mRNA polynucleotide) may comprises at least one modified or chemically modified nucleotide independently selected from the group consisting of 5-methylcytosine, isocytosine, pseudoisocytosine, 5-bromouracil, 5-propynyluracil, 6-aminopurine, 2-aminopurine, inosine, pseudouridine, 2-thiouridine, diaminopurine and 2-chloro-6-aminopurine cytosine.

In addition, suitable polynucleotide modifications include alterations in one or more nucleotides of a codon such that the codon encodes the same amino acid but is more stable than the codon found in the wild-type version of the nucleic acid. For example, an inverse relationship between the stability of RNA and a higher number cytidines (C's) and/or uridines (U's) residues has been demonstrated, and RNA devoid of C and U residues have been found to be stable to most RNases. (Heidenreich, et al. J Biol Chem 269, 2131-8 (1994)). In some embodiments, the number of C and/or U residues in an mRNA sequence is reduced. In a another embodiment, the number of C and/or U residues is reduced by substitution of one codon encoding a particular amino acid for another codon encoding the same or a related amino acid. Contemplated modifications to the mRNA nucleic acids of the present invention also include the incorporation of pseudouridines. The incorporation of pseudouridines into the mRNA nucleic acids of the present invention may enhance stability and translational capacity, as well as diminishing immunogenicity in vivo. (See, e.g., Karikó, K., et al., Molecular Therapy 16 (11): 1833-1840 (2008)). Substitutions and modifications to the nucleic acids of the present invention may be performed by methods readily known to one or ordinary skill in the art.

The constraints on reducing the number of C and U residues in a sequence will likely be greater within the coding region of an mRNA, compared to an untranslated region, (i.e., it will likely not be possible to eliminate all of the C and U residues present in the message while still retaining the ability of the message to encode the desired amino acid sequence). The degeneracy of the genetic code, however presents an opportunity to allow the number of C and/or U residues that are present in the sequence to be reduced, while maintaining the same coding capacity (i.e., depending on which amino acid is encoded by a codon, several different possibilities for modification of RNA sequences may be possible). For example, the codons for Gly can be altered to GGA or GGG instead of GGU or GGC.

The term modification also includes, for example, the incorporation of non-nucleotide linkages or modified nucleotides into the nucleic acid sequences of the present invention (e.g., modifications to one or both the 3' and 5' ends of an mRNA molecule encoding a functional protein or enzyme). Such modifications include the addition of bases to a nucleic acid sequence (e.g., the inclusion of a poly A tail or a longer poly A tail), the alteration of the 3' UTR or the 5' UTR, complexing the nucleic acid with an agent (e.g., a protein or a complementary nucleic acid molecule), and inclusion of elements which change the structure of a nucleic acid molecule (e.g., which form secondary structures).

The poly A tail is thought to stabilize natural messengers and synthetic sense RNA. Therefore, in one embodiment a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)). In one embodiment, the length of the poly A tail is at least about 20, 30, 40, 50, 60, 75, 80, 90, 100, 200, 300, 400, or at least about 500 nucleotides. In one embodiment, the length of the poly A tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of protein expression in a cell. In one embodiment, the stabilized nucleic acid molecules are sufficiently resistant to in vivo degradation (e.g., by nucleases), such that they may be delivered to the target cell without a transfer vehicle.

In one embodiment, a nucleic acid encoding a protein can be modified by the incorporation of 3' and/or 5' untranslated (UTR) sequences which are not naturally found in the wild-type nucleic acid. In one embodiment, 3' and/or 5' flanking sequence which naturally flanks an mRNA and encodes a second, unrelated protein can be incorporated into the nucleotide sequence of an mRNA molecule encoding a therapeutic or functional protein in order to modify it. For example, 3' or 5' sequences from mRNA molecules which are stable (e.g., globin, actin, GAPDH, tubulin, histone, or citric acid cycle enzymes) can be incorporated into the 3' and/or 5' region of a sense mRNA nucleic acid molecule to increase the stability of the sense mRNA molecule.

Also contemplated by the present invention are other modifications to the nucleic acid sequences made to one or both of the 3' and 5' ends of the nucleic acid. For example, the present invention contemplates modifications to one or both of the 3' and the 5' ends of the nucleic acids (e.g., mRNA) to include at least a partial sequence of a CMV immediate-early 1 (1E1) gene, or a fragment thereof to improve the nuclease resistance and/or improve the half-life of the nucleic acid. In addition to increasing the stability of the mRNA nucleic acid sequence, it has been surprisingly discovered the inclusion of a partial sequence of a CMV immediate-early 1 (IE1) gene at the 5' end enhances the translation of the mRNA and the expression of the functional protein or enzyme. Also contemplated is the inclusion of a sequence encoding human growth hormone (hGH), or a fragment thereof to one or both of the 3' and 5' ends of the nucleic acid (e.g., mRNA) to further stabilize the nucleic acid. Generally, preferred modifications improve the stability and/or pharmacokinetic properties (e.g., half-life) of the nucleic acid relative to their unmodified counterparts, and include, for example modifications made to improve such nucleic acid's resistance to in vivo nuclease digestion.

In certain embodiments, the contemplated polynucleotide modification include changes to the nucleotides to incorporate a sugar moiety having a 2'-substituent group or incorporating a bridged or locked nucleic acid (LNA) structure that can provide increased nuclease resistance. In some embodiments, a preferred modification comprises the inclusion of one or more LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the polynucleotide modifications are independently selected from, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid units as discussed by Christensen, et al., Nucl. Acids. Res. (2002) 30: 4918-4925) and 2'MOE units. In some embodiments there is only one of the above types of modifications present in the oligonucleotide of the invention. In some embodiments the polynucleotide comprises only LNA nucleotides and naturally occurring nucleotides (such as RNA), optionally with one or more modified internucleotide linkages such as phosphorothioate.

The nucleotide monomers of the polynucleotides (e.g., mRNA) described herein are coupled together via linkage groups. Suitably, each nucleotide monomer is linked to the 3' adjacent monomer via a linkage group. The person having ordinary skill in the art will understand that, in the context of the present invention, the 5' monomer at the end of an oligonucleotide does not comprise a 5' linkage group, although it may or may not comprise a 5' terminal group.

As used herein, the phrases "linkage group" and "internucleotide linkage" are intended to mean a group capable of covalently coupling together two nucleotides. Specific and preferred examples include phosphate groups and phosphorothioate groups. In certain embodiments, the polynucleotides disclosed herein have phosphorothioate internucleotide linkages at each internucleotide linkage. The nucleotide monomers of the polynucleotide of the invention or contiguous nucleotides sequence thereof are coupled together via linkage groups. Suitably each nucleotide is linked to the 3' adjacent nucleotide via a linkage group. Suitable internucleotide linkages include those listed within International Application WO 2007/031091, for example the internucleotide linkages listed on the first paragraph of page 34 of WO2007/031091.

In certain embodiments, the lipid compounds and liposomal compositions described herein are formulated as a blended formulation or composition. For example, in one embodiment, a liposomal composition comprises a blended formulation comprising a 3:1 ratio of a first lipid nanoparticle comprising HGT4003 and a second lipid nanoparticle comprising HGT4001. Accordingly, also provided herein are blended liposomal compositions and related methods for modulating the expression of a polynucleotide in one or more target cells and tissues, as disclosed for example, in U.S. Provisional Application No. 61/494,714, filed Jun. 8, 2011, the teachings of which are incorporated herein by reference in their entirety. Also contemplated are methods for modulating (e.g., increasing or synergistically increasing) the production and/or secretion of, for example, one or more functional polypeptides, proteins or enzymes that are encoded by one or more polynucleotides (e.g., mRNA) encapsulated in such blended liposomal compositions by one or more target cells, as also disclosed in U.S. Provisional Application No. 61/494,714.

In certain embodiments, the lipids and liposomal compositions provided herein are capable of modulating the expression of aberrantly expressed nucleic acids and polynucleotides in one or more target cells and tissues. Accordingly, also provided herein are methods of treating disease in a subject by administering an effective amount of the lipid compounds and/or liposomal compositions described herein to the subject. In certain embodiments, such methods may enhance (e.g., increase) the expression of a polynucleotide and/or increase the production and secretion of a functional polypeptide product in one or more target cells and tissues (e.g., hepatocytes). In some embodiments, the targeted cells or tissues aberrantly express the polynucleotide encapsulated by one or more of the lipid compounds or liposomal compositions (e.g., lipid nanoparticles) described herein. Also provided herein are methods of increasing the expression of one or more polynucleotides (e.g., mRNA) in one or more target cells, tissues and organs. Generally, such methods comprise contacting the target cells with one or more lipids and/or liposomal compositions that comprise or otherwise encapsulate one or more polynucleotides.

In certain embodiments, the lipids disclosed herein may be used as a liposome or as a component of a liposome. Specifically, in certain embodiments the compounds disclosed herein may be used as a lipid (e.g., cationic lipid) component of a liposomal composition (e.g., a lipid nanoparticle). Such liposomes may be used to encapsulate materials and facilitate the delivery of such materials to one or more target cells, tissues and organs. As used herein, the term "liposome" generally refers to a vesicle composed of lipids (e.g., amphiphilic lipids) arranged in one or more spherical bilayer or bilayers. In certain embodiments, the liposome is a lipid nanoparticle (e.g., a lipid nanoparticle comprising one or more of the cationic lipid compounds disclosed herein). Such liposomes may be unilamellar or multilamellar vesicles which have a membrane formed from a lipophilic material and an aqueous interior that contains the encapsulated materials (e.g., polynucleotides) to be delivered to one or more target cells, tissues and organs. In certain embodiments, the pharmaceutical and liposomal compositions described herein comprise one or more lipid nanoparticles. Contemplated liposomes include lipid nanoparticles. Examples of suitable lipids (e.g., cationic lipids) that may be used to form the liposomes and lipid nanoparticles contemplated hereby include one or more of the compounds disclosed herein (e.g., HGT4001, HGT4002, HGT4003, HGT4004 and/or HGT4005). Such liposomes and lipid nanoparticles may also comprise additional cationic lipids such as C12-200, DLin-KC2-DMA, DOPE, DMG-PEG-2000, non-cationic lipids, cholesterol-based lipids, helper lipids, PEG-modified lipids, as well as the phosphatidyl compounds (e.g., phosphatidylglycerol, phosphatidylcholine, phosphatidylserine, phosphatidylethanolamine, sphingolipids, cerebrosides, and gangliosides) and combinations or mixtures of the forgoing.

Several cationic lipids have been described in the literature, many of which are commercially available. In certain embodiments, such cationic lipids are included in the pharmaceutical or liposomal compositions described herein in addition to one or more of the compounds or lipids disclosed herein (e.g., HGT4003). In some embodiments, the cationic lipid N-[1-(2,3-dioleyloxy)propyl]-N,N,N-trimethylammonium chloride or "DOTMA" is used. (Felgner et al. (Proc. Nat'l Acad. Sci. 84, 7413 (1987); U.S. Pat. No. 4,897,355). DOTMA can be formulated alone or can be combined with dioleoylphosphatidylethanolamine or "DOPE" or other cationic or non-cationic lipids into a lipid nanoparticle. Other suitable cationic lipids include, for example C12-200, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. No. 5,171,678; U.S. Pat. No. 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-K-DMA", 2,2-dilinoleyl-4-dimethylaminoethyl-[1,3]-dioxolane or "DLin-K-XTC2-DMA", or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). The use of cholesterol-based cationic lipids to formulate the compositions (e.g., lipid nanoparticles) is also contemplated by the present invention. Such cholesterol-based cationic lipids can be used, either alone or in combination with other cationic or non-cationic lipids. Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335).

In addition, several reagents are commercially available to enhance transfection efficacy. Suitable examples include LIPOFECTIN (DOTMA:DOPE) (Invitrogen, Carlsbad, Calif.), LIPOFECTAMINE (DOSPA:DOPE) (Invitrogen), LIPOFECTAMINE2000. (Invitrogen), FUGENE, TRANSFECTAM (DOGS), and EFFECTENE. Also contemplated are cationic lipids such as the dialkylamino-based, imidazole-based, and guanidinium-based lipids. For example, also contemplated is the use of the cationic lipid (3S,10R,13R,17R)-10, 13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(1H-imidazol-4-yl)propanoate or "ICE", as disclosed in International Application No. PCT/US2010/058457, the teachings of which are incorporated herein by reference in their entirety.

The use and inclusion of polyethylene glycol (PEG)-modified phospholipids and derivatized lipids such as derivatized cerarmides (PEG-CER), including N-Octanoyl-Sphingosine-1-[Succinyl(Methoxy Polyethylene Glycol)-2000] (C8 PEG-2000 ceramide) in the liposomal compositions described herein is also contemplated, preferably in combination with one or more of the compounds and lipids disclosed herein. Contemplated PEG-modified lipids include, but are not limited to, a polyethylene glycol chain of up to 5 kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-polynucleotide composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in a liposomal lipid nanoparticle.

The present invention also contemplates the use of non-cationic lipids in one or more of the pharmaceutical or liposomal compositions (e.g., lipid nanoparticles). Such non-cationic lipids are preferably used in combination with one or more of the compounds and lipids disclosed herein. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), DLPE (1,2-dilauroyl-sn-glycero-3-phosphoethanolamine), DPPS (1,2-dipalmitoyl-sn-glycero-3-phospho-L-serine), 16-O-monomethyl PE, 16-O-dimethyl PE, 18-1-trans PE, 1-stearoyl-2-oleoyl-phosphatidyethanolamine (SOPE), ceramides, sphingomyelins, cholesterol, or a mixture thereof. Such non-cationic lipids may be used alone, but are preferably used in combination with other excipients, for example, one or more of the cationic lipids disclosed herein (e.g., HGT4001, HGT4002, HGT4003, HGT4004 and/or HGT4005). When used in combination with a cationic lipid, the non-cationic lipid may comprise a molar ratio of 5% to about 90%, or preferably about 10% to about 70% of the total lipid present in the lipid nanoparticle.

Also contemplated is inclusion of polymers in the lipid nanoparticles that comprise the pharmaceutical or liposomal compositions described herein. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins and polyethylenimine. Such polymers may be used alone, but are preferably used in combination with other excipients, for example, one or more of the cationic lipids disclosed herein (e.g., HGT4001, HGT4002, HGT4003, HGT4004 and/or HGT4005).

In certain embodiments, the liposomal compositions (e.g., lipid nanoparticles) are formulated and modified to facilitate the transfection (e.g., of a polynucleotide) of a target cell. In another embodiment, the liposomal compositions (e.g., lipid nanoparticles) may be selected, prepared and modified (e.g., neutralized) to optimize delivery of polynucleotides to a target cell, tissue or organ. For example, if the target cell is a hepatocyte the properties of the pharmaceutical and/or liposomal compositions (e.g., size, surface charge and/or pH) may be optimized to effectively deliver such composition (e.g., lipid nanoparticles) to the target cell or organ, reduce immune clearance and/or promote retention in that target organ. Alternatively, if the target tissue is the central nervous system the selection and preparation of the pharmaceutical and liposomal compositions must consider penetration of, and retention within the blood brain barrier and/or the use of alternate means of directly delivering such compositions (e.g., lipid nanoparticles) to such target tissue (e.g., via intracerebrovascular or intrathecal administration). In certain embodiments, the liposomal compositions described herein may be combined with a complex that facilitates the transfer of encapsulated materials (e.g., a complex which disrupt or improve the permeability of the blood brain barrier and thereby enhance the transfer of such encapsulated polynucleotides to the target cells). While the liposomal compositions described herein (e.g., lipid nanoparticles) can facilitate introduction of encapsulated materials such as one or more polynucleotides into target cells, the addition of polycations (e.g., poly L-lysine and protamine) to, for example one or more of the liposomal compositions (e.g., lipid nanoparticles) that comprise the liposomal compositions as a copolymer can also facilitate, and in some instances markedly enhance the transfection efficiency of several types of cationic liposomes by 2-28 fold in a number of cell lines both in vitro and in vivo. (See, N. J. Caplen, et al., Gene Ther. 1995; 2: 603; S. Li, et al., Gene Ther. 1997; 4, 891.)

In certain embodiments of the present invention, the pharmaceutical and liposomal compositions (e.g., lipid nanoparticles) are prepared to encapsulate one or more materials or therapeutic agents (e.g., polynucleotides). The process of incorporating a desired therapeutic agent (e.g., mRNA) into a liposome or a lipid nanoparticle is referred to herein as or "loading" or "encapsulating" (Lasic, et al., FEBS Lett., 312: 255-258, 1992). The lipid nanoparticle-loaded or -encapsulated materials (e.g., polynucleotides) may be completely or partially located in the interior space of the lipid nanoparticle, within the bilayer membrane of the lipid nanoparticle, or associated with the exterior surface of the lipid nanoparticle.

Loading or encapsulating, for example, a polynucleotide into a lipid nanoparticle may serve to protect the polynucleotide from an environment which may contain enzymes or chemicals (e.g., serum) that degrade such polynucleotides and/or systems or receptors that cause the rapid excretion of such polynucleotides. Accordingly, in some embodiments, the compositions described herein are capable of enhancing the stability of the polynucleotide(s) encapsulated thereby, particularly with respect to the environments into which such polynucleotides will be exposed. Encapsulating materials, such as for example polynucleotides into one or more of the liposomal compositions described herein (e.g., lipid nanoparticles) also facilitates the delivery of such polynucleotides into the target cells and tissues. In certain embodiments, the liposomal compositions described herein are loaded with one or more therapeutic agents prior to being modified or neutralized.

In certain embodiments, the liposomal compositions described herein (e.g., lipid nanoparticles) are prepared by combining multiple lipid components (e.g., one or more of the lipid compounds disclosed herein) with one or more polymer components. For example, a lipid nanoparticle may be prepared using HGT4003, DOPE, CHOL and DMG-PEG2000. A lipid nanoparticle may be comprised of additional lipid combinations in various ratios, including for example, HGT4001, DOPE and DMG-PEG2000. The selection of cationic lipids, non-cationic lipids and/or PEG-modified lipids which comprise the lipid nanoparticles, as well as the relative molar ratio of such lipids to each other, is based upon the characteristics of the selected lipid(s), the nature of the intended target cells or tissues and the characteristics of the materials or polynucleotides to be delivered by the lipid nanoparticle. Additional considerations include, for example, the saturation of the alkyl chain, as well as the size, surface charge, pH, pKa, fusogenicity and toxicity of the selected lipid(s).

The pharmaceutical and liposomal composition (e.g., lipid nanoparticles) for use in the present invention can be prepared by various techniques which are presently known in the art. Multi-lamellar vesicles (MLV) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Unilamellar vesicles (ULV) can then be formed by homogenization, sonication or extrusion of the multi-lamellar vesicles. In addition, unilamellar vesicles can be formed by detergent removal techniques.

In certain embodiments, the pharmaceutical and liposomal compositions of the present invention comprise a lipid nanoparticle wherein the encapsulated polynucleotide (e.g., mRNA) is associated on both the surface of the lipid nanoparticle and encapsulated within the same lipid nanoparticle. For example, during preparation of the compositions of the present invention, one or more of the lipids described herein and which are components of the liposomal compositions may associate with the polynucleotides (e.g., mRNA) through electrostatic interactions with such polynucleotides.

During the preparation of liposomal compositions described herein, water soluble carrier agents may be also encapsulated in the aqueous interior by including them in the hydrating solution, and lipophilic molecules may be incorporated into the lipid bilayer by inclusion in the lipid formulation. In the case of certain molecules (e.g., cationic or anionic lipophilic polynucleotides), loading of the polynucleotide into preformed lipid nanoparticles or liposomes may be accomplished, for example, by the methods described in U.S. Pat. No. 4,946,683, the disclosure of which is incorporated herein by reference. Following encapsulation of the polynucleotide, the lipid nanoparticles may be processed to remove un-encapsulated mRNA through processes such as gel chromatography, diafiltration or ultrafiltration. For example, if it is desirous to remove externally bound polynucleotide from the surface of the liposomal compositions (e.g., lipid nanoparticles) described herein, such lipid nanoparticles may be subject to a Diethylaminoethyl SEP-HACEL column.

There are several methods for reducing the size, or "sizing", of the liposomal compositions (e.g., lipid nanoparticles) disclosed herein, and any of these methods may generally be employed when sizing is used as part of the invention. The extrusion method is a one method of liposome sizing. (Hope, M J et al. Reduction of Liposome Size and Preparation of Unilamellar Vesicles by Extrusion Techniques. In: *Liposome Technology* (G. Gregoriadis, Ed.) Vol. 1. p 123 (1993)). The method consists of extruding liposomes through a small-pore polycarbonate membrane or an asymmetric ceramic membrane to reduce liposome sizes to a relatively well-defined size distribution. Typically, the suspension is cycled through the membrane one or more times until the desired liposome size distribution is achieved. The liposomes may be extruded through successively smaller pore membranes to achieve gradual reduction in liposome size.

A variety of alternative methods known in the art are available for sizing of a population of lipid nanoparticles. One such sizing method is described in U.S. Pat. No. 4,737,323, incorporated herein by reference. Sonicating a liposome or lipid nanoparticle suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the lipid nanoparticles may be determined by quasi-electric light scattering (QELS) as described in Bloomfield, Ann. Rev. Biophys. Bioeng., 10:421-450 (1981), incorporated herein by reference. Average lipid nanoparticle diameter may be reduced by sonication of formed lipid nanoparticles. Intermittent sonication cycles may be alternated with QELS assessment to guide efficient liposome synthesis.

Selection of the appropriate size of the liposomal compositions described herein (e.g., lipid nanoparticles) must take into consideration the site of the target cell or tissue and to some extent the application for which the lipid nanoparticle is being made. As used herein, the phrase "target cell" refers to cells to which one or more of the pharmaceutical and liposomal compositions described herein are to be directed or targeted. In some embodiments, the target cells comprise a particular tissue or organ. In some embodiments, the target cells are deficient in a protein or enzyme of interest. For example, where it is desired to deliver a polynucleotide to a hepatocyte, the hepatocyte represents the target cell. In some embodiments, the pharmaceutical or liposomal compositions (and for example the polynucleotide materials encapsulated therein) of the present invention transfect the target cells on a discriminatory basis (i.e., do not transfect non-target cells). The compositions and methods of the present invention may be prepared to preferentially target a variety of target cells, which include, but are not limited to, hepatocytes, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Following transfection of one or more target cells by, for example, the polynucleotides encapsulated in the one or more liposomal compositions disclosed herein, the production of the product (e.g., a polypeptide or protein) encoded by such polynucleotide may be preferably stimulated and the capability of such target cells to express the polynucleotide and produce, for example, a polypeptide or protein of interest is enhanced. For example, transfection of a target cell by one or more liposomal compositions encapsulating mRNA will enhance (i.e., increase) the production of the protein or enzyme encoded by such mRNA.

In some embodiments, it may be desirable to limit transfection of the polynucleotides to certain cells or tissues. For example, the liver represents an important target organ for the compositions of the present invention in part due to its central role in metabolism and production of proteins and accordingly diseases which are caused by defects in liver-specific gene products (e.g., the urea cycle disorders) may benefit from specific targeting of cells (e.g., hepatocytes). Accordingly, in certain embodiments of the present invention, the structural characteristics of the target tissue may be exploited to direct the distribution of the pharmaceutical and liposomal compositions of the present invention (e.g., an HGT4001-based lipid nanoparticle) to such target tissues. For example, to target hepatocytes one or more of the lipid nanoparticles that comprise the pharmaceutical or liposomal compositions described herein may be sized or their surface charge modified such that they are able to readily penetrate such endothelial fenestrations to reach the target hepatocytes. Alternatively, a lipid nanoparticle may be sized or its surface charge modified such that the dimensions of the liposome are of a sufficient diameter to limit or expressly avoid distribution into certain cells or tissues. For example, lipid nanoparticles that comprise the pharmaceutical and liposomal compositions described herein may be sized such that their dimensions are larger than the fenestrations of the endothelial layer lining hepatic sinusoids to thereby limit distribution of the liposomal lipid nanoparticle to hepatocytes. In such an embodiment, large liposomal compositions (e.g., lipid nanoparticles) will not easily penetrate the endothelial fenestrations, and would instead be cleared by the macrophage Kupffer cells that line the liver sinusoids. Sizing of, for example, the liposomal composition (e.g., lipid nanoparticles) may therefore provide an opportunity to further manipulate and precisely control the degree to which expression of the encapsulated polynucleotides may be enhanced in one or more target cells. Generally, the size of at least one of the lipid nanoparticles that comprise the pharmaceutical and liposomal compositions of the present invention is within the range of about 25 to 250 nm, preferably less than about 250 nm, 175 nm, 150 nm, 125 nm, 100 nm, 75 nm, 50 nm, 25 nm or 10 nm.

Similarly, the compositions of the present invention may be prepared to preferentially distribute to other target tissues, cells or organs, such as the heart, lungs, kidneys, spleen. For example, the lipid nanoparticles of the present invention may be prepared to achieve enhanced delivery to the target cells and tissues. Accordingly, the compositions of the present invention may be enriched with additional cationic, non-cationic and PEG-modified lipids to further target tissues or cells.

In some embodiments, the lipid compounds and the pharmaceutical and liposomal compositions described herein (e.g., HGT4002-based lipid nanoparticles) distribute to the cells and tissues of the liver to enhance the delivery, transfection and the subsequent expression of the polynucleotides (e.g., mRNA) encapsulated therein by the cells and tissues of the liver (e.g., hepatocytes) and the corresponding production of the polypeptide or protein encoded by such polynucleotide. While such compositions may preferentially distribute into the cells and tissues of the liver, the therapeutic effects of the expressed polynucleotides and the subsequent production of a protein encoded thereby need not be limited to the target cells and tissues. For example, the targeted hepatocytes may function as a "reservoir" or "depot" capable of expressing or producing, and systemically or peripherally excreting a functional protein or enzyme, as disclosed for example, in International Application No. PCT/US2010/058457 and in U.S. Provisional Application No. 61/494,881, the teachings of which are both incorporated herein by reference in their entirety. It should be understood that the lipid compositions, liposomal vehicles and related methods disclosed herein may be used to target any cells and/or tissues such that those targeted cells and/or tissues function as a reservoir or depot capable of expressing, producing or otherwise secreting a functional enzyme or protein. For example, the compositions disclosed herein may preferentially target and distribute to the cells and tissues of the lung, heart, kidneys, liver and/or spleen such that those cells are rendered capable of expressing (e.g., translating) the functional protein or enzyme that is encoded by the polynucleotide (e.g., an mRNA polynucleotide) encapsulated in the liposomal vehicles (e.g., lipid nanoparticles) disclosed herein. Accordingly, in certain embodiments of the present invention the one or more of the lipid nanoparticles that comprise the pharmaceutical and liposomal compositions described herein (e.g., HGT4005-based lipid nanoparticles) may target hepatocytes and/or preferentially distribute to the cells and tissues of the liver upon delivery. Following the transfection of the target hepatocytes by the polynucleotide encapsulated in one or more of such lipid nanoparticles, such polynucleotides are expressed (e.g., translated) and a functional product (e.g., a polypeptide or protein) is excreted and systemically distributed, where such functional product may exert a desired therapeutic effect.

The polynucleotides encapsulated in one or more of the lipid compounds or liposomal compositions described herein can be delivered to and/or transfect targeted cells or tissues. In some embodiments, the encapsulated polynucleotides are capable of being expressed and functional polypeptide products produced (and in some instances excreted) by the target cell, thereby conferring a beneficial property to, for example the target cells or tissues. Such encapsulated polynucleotides may encode, for example, a hormone, enzyme, receptor, polypeptide, peptide or other protein of interest. In certain embodiments, such encapsulated polynucleotides may also encode a small interfering RNA (siRNA) or antisense RNA for the purpose of modulating or otherwise decreasing or eliminating the expression of an endogenous nucleic acid or gene. In certain embodiments such encapsulated polynucleotides may be natural or recombinant in nature and may exert their therapeutic activity using either sense or antisense mechanisms of action (e.g., by modulating the expression of a target gene or nucleic acid).

In some embodiments, the encapsulated polynucleotides (e.g., mRNA encoding a deficient protein) may optionally include chemical or biological modifications which, for example, improves the stability and/or half-life of such polynucleotide or which improves or otherwise facilitates translation of such polynucleotide.

Also contemplated by the present invention is the co-delivery of one or more unique polynucleotides to target cells by the lipids or liposomal compositions described herein, for example, by combining two unique therapeutic agents or polynucleotides into a single lipid nanoparticle. Also contemplated is the delivery of one or more encapsulated polynucleotides to one or more target cells to treat a single disorder or deficiency, wherein each such polynucleotide functions by a different mechanism of action. For example, the pharmaceutical or liposomal compositions of the present invention may comprise a first polynucleotide which, for example, is encapsulated in a lipid nanoparticle and intended to correct an endogenous protein or enzyme deficiency, and a second polynucleotide intended to deactivate or "knock-down" a malfunctioning endogenous polynucleotide and its protein or enzyme product. Such encapsulated polynucleotides may encode, for example mRNA and siRNA.

While in vitro transcribed polynucleotides (e.g., mRNA) may be transfected into target cells, such polynucleotides may be readily and efficiently degraded by the cell in vivo, thus rendering such polynucleotides ineffective. Moreover, some polynucleotides are unstable in bodily fluids (particularly human serum) and can be degraded or digested even before reaching a target cell. In addition, within a cell, a natural mRNA can decay with a half-life of between 30 minutes and several days. Accordingly, in certain embodiments, the encapsulated polynucleotides provided herein, and in particular the mRNA polynucleotides provided herein, preferably retain at least some ability to be expressed or translated, to thereby produce a functional protein or enzyme within one or more target cells.

As used herein, the term "subject" refers to any animal (e.g., a mammal), including, but not limited to, humans, non-human primates, rodents, and the like, to which the lipids, compounds or liposomal compositions and methods of the present invention may be administered. Typically, the terms "subject" and "patient" are used interchangeably herein in reference to a human subject.

The ability of the lipids, compounds and/or liposomal compositions described herein (e.g., lipid nanoparticles) to modulate or enhance the expression of encapsulated polynucleotides and the production of a polypeptide or protein provides novel and more efficient means of effectuating the in vivo production of polypeptides and proteins for the treatment of a host of diseases or pathological conditions. Such lipid nanoparticle compositions are particularly suitable for the treatment of diseases or pathological conditions associated with the aberrant expression of nucleic acids encoding a protein or enzyme. For example, the successful delivery of polynucleotides such as mRNA to target organs such as the liver and in particular, to hepatocytes, can be used for the treatment and the correction of in-born errors of metabolism that are localized to the liver. Accordingly, the lipids, compounds, liposomal compositions and related methods described herein may be employed to treat a wide range of diseases and pathological conditions, in particular those diseases which are due to protein or enzyme deficiencies. The polynucleotides encapsulated by the lipids or liposomal compositions described herein (e.g., HGT4004-based lipid nanoparticles) may encode a functional product (e.g., a protein, enzyme, polypeptide, peptide, functional RNA, and/or antisense molecule), and preferably encodes a product whose in vivo production is desired.

The lipids, liposomal compositions and related methods of the present invention are broadly applicable to the delivery of therapeutic agents such as polynucleotides, and in particular mRNA, to treat a number of disorders. In particular, such compounds, compositions and related methods of the present invention are suitable for the treatment of diseases or disorders relating to the deficiency of proteins and/or enzymes. In certain embodiments, the lipid nanoparticle-encapsulated polynucleotides encode functional proteins or enzymes that are excreted or secreted by one or more target cells into the surrounding extracellular fluid (e.g., mRNA encoding hormones and neurotransmitters). Alternatively, in another embodiment, the polynucleotides encapsulated by the lipids and/or liposomal compositions of the present invention encode functional proteins or enzymes that remain in the cytosol of one or more target cells (e.g., mRNA encoding an enzyme associated with urea cycle or lysosomal storage metabolic disorders). Other disorders for which the lipids, compounds, liposomal compositions and related methods of the present invention are useful include, but are not limited to, disorders such as SMN1-related spinal muscular atrophy (SMA); amyotrophic lateral sclerosis (ALS); GALT-related galactosemia; Cystic Fibrosis (CF); SLC3A1-related disorders including cystinuria; COL4A5-related disorders including Alport syndrome; galactocerebrosidase deficiencies; X-linked adrenoleukodystrophy and adrenomyeloneuropathy; Friedreich's ataxia; Pelizaeus-Merzbacher disease; TSC1 and TSC2-related tuberous sclerosis; Sanfilippo B syndrome (MPS MB); CTNS-related cystinosis; the FMR1-related disorders which include Fragile X syndrome, Fragile X-Associated Tremor/Ataxia Syndrome and Fragile X Premature Ovarian Failure Syndrome; Prader-Willi syndrome; Fabry disease; hereditary hemorrhagic telangiectasia (AT); Niemann-Pick disease Type C1; the neuronal ceroid lipofuscinoses-related diseases including Juvenile Neuronal Ceroid Lipofuscinosis (JNCL), Juvenile Batten disease, Santavuori-Haltia disease, Jansky-Bielschowsky disease, and PTT-1 and TPP1 deficiencies; EIF2B1, EIF2B2, EIF2B3, EIF2B4 and EIF2B5-related childhood ataxia with central nervous system hypomyelination/vanishing white matter; CACNA1A and CACNB4-related Episodic Ataxia Type 2; the MECP2-related disorders including Classic Rett Syndrome, MECP2-related Severe Neonatal Encephalopathy and PPM-X Syndrome; CDKL5-related Atypical Rett Syndrome; Kennedy's disease (SBMA); Notch-3 related cerebral autosomal dominant arteriopathy with subcortical infarcts and leukoencephalopathy (CADASIL); SCN1A and SCN1B-related seizure disorders; the Polymerase G-related disorders which include Alpers-Huttenlocher syndrome, POLG-related sensory ataxic neuropathy, dysarthria, and ophthalmoparesis, and autosomal dominant and recessive progressive external ophthalmoplegia with mitochondrial DNA deletions; X-Linked adrenal hypoplasia; X-linked agammaglobulinemia; and Wilson's disease. In certain embodiments, the polynucleotides, and in particular mRNA, of the present invention may encode functional proteins or enzymes. For example, the compositions of the present invention may include mRNA encoding ornithine transcarbamylase (OTC), carbamoyl-phosphate synthetase 1 (CP S1), argininosuccinate synthetase (ASS1), argininosuccinate lyase (ASL) or arginase 1 (ARG1), cystic fibrosis transmembrane conductance regulator (CFTR), acid alpha glucosidase, arylsulfatase A, alpha galactosidase A, erythropoietin, α1-antitrypsin, carboxypeptidase N, alpha-L-iduronidase, iduronate-2-sulfatase, iduronate sulfatase, N-acetylglucosamine-1-phosphate transferase, N-acctylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, heparin-N-sulfatase, lysosomal acid lipase, hyaluronidase, galactocerebrosidase, human growth hormone, survival motor neuron, Factor VIII, Factor IX or low density lipoprotein receptors.

In one embodiment, the mRNA encodes a protein or an enzyme selected from the group consisting of human growth hormone, erythropoietin, α1-antitrypsin, acid alpha glucosidase, arylsulfatase A, carboxypeptidase N, α-galactosidase A, alpha-L-iduronidase, iduronate-2-sulfatase, iduronate sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, heparin-N-sulfatase, lysosomal acid lipase, hyaluronidase, galactocerebrosidase, ornithine transcarbamylase (OTC), carbamoyl-phosphate synthetase 1 (CPS1), argininosuccinate synthetase (ASS1), argininosuccinate lyase (ASL), arginase 1 (ARG1), cystic fibrosis transmembrane conductance regulator (CFTR), survival motor neuron (SMN), Factor VIII, Factor IX and low density lipoprotein receptors (LDLR).

The lipids, compounds and liposomal compositions described herein may be administered to a subject. In some embodiments, the compositions are formulated in combination with one or more additional polynucleotides, carriers, targeting ligands or stabilizing reagents or other suitable excipients. Techniques for formulation and administration of drugs may be found in "Remington's Pharmaceutical Sciences," Mack Publishing Co., Easton, Pa., latest edition.

The lipids and liposomal compositions (e.g., lipid nanoparticles) of the present invention may be administered and dosed in accordance with current medical practice, taking into account the clinical condition of the subject, the nature of the encapsulated materials, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient expression of the one or more polynucleotides in the target cells.

Suitable routes of administration of the lipids, compounds and liposomal compositions disclosed herein include, for example, oral, rectal, vaginal, transmucosal, or intestinal administration; parenteral delivery, including intramuscular, subcutaneous, intramedullary injections, as well as intrathecal, intracerebroventricular, direct intraventricular, intravenous, intraperitoneal, intranasal, or intraocular injections or infusions. In certain embodiments, the administration of the lipids, compounds or liposomal compositions (e.g., lipid nanoparticle) described herein to a subject facilitates the contacting of such compounds or compositions to one or more target cells, tissues or organs.

Alternately, the lipids, compounds and liposomal compositions of the present invention may be administered in a local rather than systemic manner, for example, via injection or infusion of the liposomal compositions directly into a targeted tissue, preferably in a depot or sustained release formulation, such that the contacting of the targeted cells with the constituent lipid nanoparticles may be further facilitated. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing the lipid compounds of the present invention complexed with therapeutic molecules or ligands can even be surgically administered, for example in association with a polymer or other structure or substance that can allow the compositions to diffuse from the site of implantation to surrounding cells. Alternatively, such compositions can be applied surgically without the use of polymers or supports.

The lipids and liposomal compositions of the present invention (e.g., lipid nanoparticles that have been neutralized or otherwise modified in accordance with the teachings provided herein) are preferably stable (e.g., when stored under refrigerated conditions for at least one year). In certain embodiments, the stability of the lipids and liposomal compositions provided herein may be extended by lyophilizing such compositions. Accordingly, also contemplated herein are lyophilized liposomal compositions comprising one or more of the lipid compounds disclosed herein and related methods for the use of such lyophilized compositions as disclosed for example, in U.S. Provisional Application No. 61/494,882, filed Jun. 8, 2011, the teachings of which are incorporated herein by reference in their entirety.

In certain embodiments, the compositions of the present invention are formulated such that they are suitable for extended-release of the, for example, polynucleotides or nucleic acids encapsulated therein. Such extended-release compositions may be conveniently administered to a subject at extended dosing intervals. For example, in certain embodiments, the compositions of the present invention are administered to a subject twice day, daily or every other day. In a certain embodiments, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and lipid nanoparticles which are formulated for depot administration (e.g., intramuscularly, subcutaneously, intravitreally) to either deliver or release a polynucleotide (e.g., mRNA) over extended periods of time. Preferably, the extended-release means employed are combined with modifications (e.g., chemical modifications) introduced into the polynucleotides to enhance stability.

While certain compounds, compositions and methods of the present invention have been described with specificity in accordance with certain embodiments, the following examples serve only to illustrate the compounds of the invention and are not intended to limit the same. Each of the publications, reference materials and the like referenced herein to describe the background of the invention and to provide additional detail regarding its practice are hereby incorporated by reference in their entirety.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1

The present example illustrates that HGT4002-based lipid nanoparticles may be reductively neutralized after having been loaded with mRNA polynucleotide constructs. The HGT4002-based lipid nanoparticles were formed via standard ethanol injection methods as described below. (Ponsa, et al., *Int. J. Pharm.* (1993) 95: 51-56.) Ethanolic stock solutions of the lipids were prepared ahead of time at a concentration of 50 mg/mL and stored at −20° C.

Codon-optimized firefly luciferase (CO-FFL) mRNA was synthesized by in vitro transcription from a plasmid DNA template, which was followed by the addition of a 5' cap structure (Cap1) (Fechter, P. et al., *J. Gen. Virology* (2005) 86: 1239-1249) and a 3' poly(A) tail of approximately 200 nucleotides in length as determined by gel electrophoresis. The 5' and 3' untranslated regions present in each mRNA product are represented as X and Y, respectively in SEQ ID NO: 1, as indicated below.

```
Codon-Optimized Firefly Luciferase (FFL) mRNA:
                                    SEQ ID NO: 1
XAUGGAAGAUGCCAAAAACAUUAAGAAGGGCCCAGCGCCAUUCUACCCA

CUCGAAGACGGGACCGCCGGCGAGCAGCUGCACAAAGCCAUGAAGCGCU

ACGCCCUGGUGCCCGGCACCAUCGCCUUUACCGACGCACAUAUCGAGGU

GGACAUUACCUACGCCGAGUACUUCGAGAUGAGCGUUCGGCUGGCAGAA

GCUAUGAAGCGCUAUGGGCUGAAUACAAACCAUCGGAUCGUGGUGUGCA

GCGAGAAUAGCUUGCAGUUCUUCAUGCCCGUGUUGGGUGCCCUGUUCAU

CGGUGUGGCUGUGGCCCCAGCUAACGACAUCUACAACGAGCGCGAGCUG

CUGAACAGCAUGGGCAUCAGCCAGCCCACCGUCGUAUUCGUGAGCAAGA

AAGGGCUGCAAAAGAUCCUCAACGUGCAAAAGAAGCUACCGAUCAUACA

AAAGAUCAUCAUGGAUAGCAAGACCGACUACCAGGGCUUCCAAAGC

AUGUACACCUUCGUGACUUCCCAUUUGCCACCCGGCUUCAACGAGUACG

ACUUCGUGCCCGAGAGCUUCGACCGGGACAAAACCAUCGCCCUGAUCAU

GAACAGUAGUGGCAGUACCGGAUUGCCCAAGGGCGUAGCCCUACCGCAC

CGCACCGCUUGUGUCCGAUUCAGUCAUGCCCGCGACCCCAUCUUCGGCA

ACCAGAUCAUCCCCGACACCGCUAUCCUCAGCGUGGUGCCAUUUCACCA

CGGCUUCGGCAUGUUCACCACGCUGGGCUACUUGAUCUGCGGCUUUCGG

GUCGUGCUCAUGUACCGCUUCGAGGAGGAGCUAUUCUUGCGCAGCUUGC

AAGACUAUAAGAUUCAAUCUGCCCUGCUGGUGCCCACACUAUUUAGCUU

CUUCGCUAAGAGCACUCUCAUCGACAAGUACGACCUAAGCAACUUGCAC

GAGAUCGCCAGCGGCGGGGCGCCGCUCAGCAAGGAGGUAGGUGAGGCCG

UGGCCAAACGCUUCCACCUACCAGGCAUCCGCCAGGGCUACGGCCUGAC

AGAAACAACCAGCGCCAUUCUGAUCACCCCCGAAGGGGACGACAAGCCU

GGCGCAGUAGGCAAGGUGGUGCCCUUCUUCGAGGCUAAGGUGGUGGACU

UGGACACCGGUAAGACACUGGGUGUGAACCAGCGCGGCGAGCUGUGCGU

CCGUGGCCCCAUGAUCAUGAGCGGCUACGUUAACAACCCCGAGGCUACA

AACGCUCUCAUCGACAAGGACGGCUGGCUGCACAGCGGCGACAUCGCCU

ACUGGGACGAGGACGAGCACUUCUUCAUCGUGGACCGGCUGAAGAGCCU

GAUCAAAUACAAGGGCUACCAGGUAGCCCCAGCCGAACUGGAGAGCAUC

CUGCUGCAACACCCCAACAUCUUCGACGCCGGGGUCGCCGGCCUGCCCG

ACGACGAUGCCGGCGAGCUGCCCGCCGCAGUCGUCGUGCUGGAACACGG

UAAAACCAUGACCGAGAAGGAGAUCGUGGACUAUGUGGCCAGCCAGGUU

ACAACCGCCAAGAAGCUGCGCGGUGGUGUUGUGUUCGUGGACGAGGUGC

CUAAAGGACUGACCGGCAAGUUGGACGCCCGCAAGAUCCGCGAGAUUCU

CAUUAAGGCCAAGAAGGGCGGCAAGAUCGCCGUGUAY

X =
                                    (SEQ ID NO: 2)
GGGAUCCUACC

Y =
                                    (SEQ ID NO: 3)
UUUGAAUU
```

Next, 0.25 mg of the FFL mRNA was denatured by heating it at 70° C. for 5 minutes using a heat block. A 3 mL volume of an aqueous buffered solution (10 mM citrate/150 mM NaCl, pH 4.5) was prepared and heated in a 15 mL RNase-Free conical tube by placing the tube in a heated water bath, and into which was followed by the instant addition of the FFL mRNA into the heated aqueous buffered solution to achieve a final FFL mRNA concentration of 0.25 mg/3 mL.

All mRNA concentrations were determined via the Ribogreen assay (Invitrogen). Encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

To prepare the lipid nanoparticles, aliquots of 50 mg/mL ethanolic solutions of HGT4002, DOPE, cholesterol and DMG-PEG2000 were mixed as indicated below in Table 1, heated to ensure dissolution and diluted with ethanol. The resulting lipid solution is suitable for 0.25 mg mRNA at N/P ratio of 4.

TABLE 1

| Lipid Components | Molar Ratio | MW | μmol | Weight (mg) | Volume (μL) |
|---|---|---|---|---|---|
| DMG-PEG2000 | 6 | 2509.19 | 1.04 | 2.6 | 52.2 |
| HGT4002 | 18 | 506 | 3.12 | 1.6 | 31.6 |
| CHOL | 20 | 386.65 | 3.47 | 1.3 | 26.8 |
| DOPE | 56 | 744.03 | 9.71 | 7.2 | 144.4 |
| Total | 100 | — | 17.33 | 12.8 | 255.0 |

0.5 mL of the ethanolic lipid solution was injected rapidly into the heated (70° C.) aqueous mRNA/buffer solution, shaken and the resulting suspension quickly returned to the 70° C. water bath. The resulting nanoparticle suspension was concentrated, re-suspended in a sodium borate buffer (pH 8.0), passed through MUSTANG Q membranes (Pall Life Sciences), was filtered and diafiltrated with 1× PBS (pH 7.4) and further concentrated. The $Z_{ave}$ of the resulting lipid nanoparticles was 159.4 nm ($Dv_{(50)}$=147 nm; $Dv_{(90)}$=299 nm) and the average Zeta potential was 28.0 mV. The lipid nanoparticles demonstrated an encapsulation efficiency of approximately 82%.

The lipid nanoparticles were then exposed to aqueous solutions comprising the reducing agent β-mercaptoethanol (β-ME) and the Zeta potential of the lipid nanoparticle assessed. Exposure of the lipid nanoparticles to 250 μL (100×) of a β-ME solution for one hour caused the Zeta potential of the lipid nanoparticle to be reduced to 15.8 mV. Exposure of the lipid nanoparticles to 250 μL (100×) of a β-ME solution for three hours caused the Zeta potential of the lipid nanoparticle to be reduced to −0.26 mV. Exposure of the lipid nanoparticles to 25 μL (10×) of a β-ME solution for twenty two hours caused the Zeta potential of the lipid nanoparticle to be reduced to 1.59 mV.

The foregoing supports the conclusion that upon exposure to a reducing agent, the charge (i.e., Zeta potential) of HGT4002-based lipid nanoparticles can be modulated, and in certain instances neutralized.

Example 2

The present example illustrates that HGT4002-based lipid nanoparticles may be reductively neutralized after having been loaded with mRNA polynucleotide constructs. The HGT4002-based lipid nanoparticles were formed via standard ethanol injection methods as described below. (Ponsa, et al., Int. J. Pharm. (1993) 95: 51-56.) Ethanolic stock solutions of the lipids were prepared ahead of time at a concentration of 50 mg/mL and stored at −20° C.

Codon-optimized firefly luciferase (CO-FFL) mRNA was synthesized by in vitro transcription from a plasmid DNA template, which was followed by the addition of a 5′ cap structure (Cap1) (Fechter, P. et al., J. Gen. Virology (2005) 86: 1239-1249) and a 3′ poly(A) tail of approximately 200 nucleotides in length as determined by gel electrophoresis. The 5′ and 3′ untranslated regions present in each mRNA product are represented as X and Y, respectively in SEQ ID NO: 1, as indicated below.

```
Codon-Optimized Firefly Luciferase (FFL) mRNA:
                                         SEQ ID NO: 1
XAUGGAAGAUGCCAAAAACAUUAAGAAGGGCCCAGCGCCAUUCUACCCA

CUCGAAGACGGGACCGCCGGCGAGCAGCUGCACAAAGCCAUGAAGCGCU

ACGCCCUGGUGCCCGGCACCAUCGCCUUUACCGACGCACAUAUCGAGGU

GGACAUUACCUACGCCGAGUACUUCGAGAUGAGCGUUCGGCUGGCAGAA

GCUAUGAAGCGCUAUGGGCUGAAUACAAACCAUCGGAUCGUGGUGUGCA

GCGAGAAUAGCUUGCAGUUCUUCAUGCCCGUGUUGGGUGCCCUGUUCAU

CGGUGUGGCUGUGGCCCCAGCUAACGACAUCUACAACGAGCGCGAGCUG

CUGAACAGCAUGGGCAUCAGCCAGCCCACCGUCGUAUUCGUGAGCAAGA

AAGGGCUGCAAAAGAUCCUCAACGUGCAAAAGAAGCUACCGAUCAUACA

AAAGAUCAUCAUCAUGGAUAGCAAGACCGACUACCAGGGCUUCCAAAGC

AUGUACACCUUCGUGACUUCCCAUUUGCCACCCGGCUUCAACGAGUACG

ACUUCGUGCCCGAGAGCUUCGACCGGGACAAAACCAUCGCCCUGAUCAU

GAACAGUAGUGGCAGUACCGGAUUGCCCAAGGGCGUAGCCCUACCGCAC

CGCACCGCUUGUGUCCGAUUCAGUCAUGCCCGCGACCCCAUCUUCGGCA

ACCAGAUCAUCCCCGACACCGCUAUCCUCAGCGUGGUGCCAUUUCACCA

CGGCUUCGGCAUGUUCACCACGCUGGGCUACUUGAUCUGCGGCUUUCGG

GUCGUGCUCAUGUACCGCUUCGAGGAGGAGCUAUUCUUGCGCAGCUUGC

AAGACUAUAAGAUUCAAUCUGCCCUGCUGGUGCCCACACUAUUUAGCUU

CUUCGCUAAGAGCACUCUCAUCGACAAGUACGACCUAAGCAACUUGCAC

GAGAUCGCCAGCGGCGGGGCGCCGCUCAGCAAGGAGGUAGGUGAGGCCG

UGGCCAAACGCUUCCACCUACCAGGCAUCCGCCAGGGCUACGGCCUGAC

AGAAACAACCAGCGCCAUUCUGAUCACCCCCGAAGGGGACGACAAGCCU

GGCGCAGUAGGCAAGGUGGUGCCCUUCUUCGAGGCUAAGGUGGUGGACU

UGGACACCGGUAAGACACUGGGUGUGAACCAGCGCGGCGAGCUGUGCGU

CCGUGGCCCCAUGAUCAUGAGCGGCUACGUUAACAACCCCGAGGCUACA

AACGCUCUCAUCGACAAGGACGGCUGGCUGCACAGCGGCGACAUCGCCU

ACUGGGACGAGGACGAGCACUUCUUCAUCGUGGACCGGCUGAAGAGCCU

GAUCAAAUACAAGGGCUACCAGGUAGCCCCAGCCGAACUGGAGAGCAUC

CUGCUGCAACACCCCAACAUCUUCGACGCCGGGGUCGCCGGCCUGCCCG

ACGACGAUGCCGGCGAGCUGCCCGCCGCAGUCGUCGUGCUGGAACACGG

UAAAACCAUGACCGAGAAGGAGAUCGUGGACUAUGUGGCCAGCCAGGUU

ACAACCGCCAAGAAGCUGCGCGGUGGUGUUGUGUUCGUGGACGAGGUGC

CUAAAGGACUGACCGGCAAGUUGGACGCCCGCAAGAUCCGCGAGAUUCU

CAUUAAGGCCAAGAAGGGCGGCAAGAUCGCCGUGUAY

X =
                                         (SEQ ID NO: 2)
GGGAUCCUACC

Y =
                                         (SEQ ID NO: 3)
UUUGAAUU
```

Next, 0.25 mg of the FFL mRNA was denatured by heating it at 70° C. for 5 minutes using a heat block. A 2 mL volume of an aqueous buffered solution (10 mM citrate/150 mM NaCl, pH 4.5) was prepared and heated in an RNase-Free conical tube by placing the tube in a heated water bath, and into which was followed by the instant addition of the FFL mRNA into the heated aqueous buffered solution to achieve a final FFL mRNA concentration of 0.25 mg/2 mL.

All mRNA concentrations were determined via the Ribogreen assay (Invitrogen). Encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

To prepare the lipid nanoparticles, aliquots of 50 mg/mL ethanolic solutions of HGT4002, DOPE, cholesterol and DMG-PEG2000 were mixed as indicated in Table 2 below, heated to ensure dissolution and diluted with ethanol. The resulting lipid solution is suitable for 0.25 mg mRNA at N/P ratio of 4.

TABLE 2

| Lipid Components | Molar Ratio | MW | µmol | Weight (mg) | Volume (µL) |
|---|---|---|---|---|---|
| DMG-PEG2000 | 6 | 2509.19 | 1.04 | 2.6 | 52.2 |
| HGT4002 | 18 | 506 | 3.12 | 1.6 | 31.6 |
| CHOL | 20 | 386.65 | 3.47 | 1.3 | 26.8 |
| DOPE | 56 | 744.03 | 9.71 | 7.2 | 144.4 |
| Total | 100 | — | 17.33 | 12.8 | 255.0 |

0.5 mL of the ethanolic lipid solution was injected rapidly into the heated (70° C.) aqueous mRNA/buffer solution, shaken and the resulting suspension quickly returned to the 70° C. water bath. The resulting nanoparticle suspension was concentrated, re-suspended in a sodium borate buffer (pH 8.0), passed through MUSTANG Q membranes (Pall Life Sciences), was filtered and diafiltrated with 1× PBS (pH 7.4) and further concentrated. The $Z_{ave}$ of the resulting lipid nanoparticles was 115.5 nm ($Dv_{(50)}$=92.1 nm; $Dv_{(90)}$=162 nm) and the average Zeta potential was 29.1 mV. The lipid nanoparticles demonstrated an encapsulation efficiency of approximately 80%.

The lipid nanoparticles were then exposed to aqueous solutions comprising the reducing agent β-mercaptoethanol (β-ME) and the Zeta potential of the lipid nanoparticle assessed. Exposure of the lipid nanoparticles to 25 µL (10×) of a β-ME solution for eighteen hours caused the Zeta potential of the lipid nanoparticle to be reduced to −3.50 mV. Exposure of the lipid nanoparticles to 250 µL (100×) of a β-ME solution for one hour caused the Zeta potential of the lipid nanoparticle to be reduced to 14.8 mV. Exposure of the lipid nanoparticles to 250 µL (100×) of a β-ME solution for two and one-half hours caused the Zeta potential of the lipid nanoparticle to be reduced to 2.85 mV. Exposure of the lipid nanoparticles to 250 µL (100×) of a β-ME solution for three hours caused the Zeta potential of the lipid nanoparticle to be reduced to −3.40 mV. The foregoing supports the conclusion that by exposing charged lipid nanoparticles to a reducing agent, the charge (i.e., Zeta potential) of the lipid nanoparticle can be modulated, and in certain instances neutralized.

Example 3

The present example further illustrates that HGT4002-based lipid nanoparticles may be reductively neutralized after having been loaded with mRNA polynucleotide constructs. The HGT4002-based lipid nanoparticles were formed via standard ethanol injection methods as described below. (Ponsa, et al., Int. J. Pharm. (1993) 95: 51-56.) Ethanolic stock solutions of the lipids were prepared ahead of time at a concentration of 50 mg/mL and stored at −20° C.

Codon-optimized firefly luciferase (CO-FFL) mRNA was synthesized by in vitro transcription from a plasmid DNA template, which was followed by the addition of a 5' cap structure (Cap1) (Fechter, P. et al., J. Gen. Virology (2005) 86: 1239-1249) and a 3' poly(A) tail of approximately 200 nucleotides in length as determined by gel electrophoresis. The 5' and 3' untranslated regions present in each mRNA product are represented as X and Y, respectively in SEQ ID NO: 1, as indicated below.

Codon-Optimized Firefly Luciferase (FFL) mRNA:
SEQ ID NO: 1
XAUGGAAGAUGCCAAAAACAUUAAGAAGGGCCCAGCGCCAUUCUACCCA
CUCGAAGACGGGACCGCCGGCGAGCAGCUGCACAAAGCCAUGAAGCGCU
ACGCCCUGGUGCCCGGCACCAUCGCCUUUACCGACGCACAUAUCGAGGU
GGACAUUACCUACGCCGAGUACUUCGAGAUGAGCGUUCGGCUGGCAGAA
GCUAUGAAGCGCUAUGGGCUGAAUACAAACCAUCGGAUCGUGGUGUGCA
GCGAGAAUAGCUUGCAGUUCUUCAUGCCCGUGUUGGGUGCCCUGUUCAU
CGGUGUGGCUGUGGCCCCAGCUAACGACAUCUACAACGAGCGCGAGCUG
CUGAACAGCAUGGGCAUCAGCCAGCCCACCGUCGUAUUCGUGAGCAAGA
AAGGGCUGCAAAAGAUCCUCAACGUGCAAAAGAAGCUACCGAUCAUACA
AAAGAUCAUCAUCAUGGAUAGCAAGACCGACUACCAGGGCUUCCAAAGC
AUGUACACCUUCGUGACUUCCCAUUUGCCACCCGGCUUCAACGAGUACG
ACUUCGUGCCCGAGAGCUUCGACCGGGACAAAACCAUCGCCCUGAUCAU
GAACAGUAGUGGCAGUACCGGAUUGCCCAAGGGCGUAGCCCUACCGCAC
CGCACCGCUUGUGUCCGAUUCAGUCAUGCCCGCGACCCCAUCUUCGGCA
ACCAGAUCAUCCCCGACACCGCUAUCCUCAGCGUGGUGCAUUUCACCA
CGGCUUCGGCAUGUUCACCACGCUGGGCUACUUGAUCUGCGGCUUUCGG
GUCGUGCUCAUGUACCGCUUCGAGGAGGAGCUAUUCUUGCGCAGCUUGC
AAGACUAUAAGAUUCAAUCUGCCCUGCUGGUGCCCACACUAUUUAGCUU
CUUCGCUAAGAGCACUCUCAUCGACAAGUACGACCUAAGCAACUUGCAC
GAGAUCGCCAGCGGCGGGCGCCGCUCAGCAAGGAGGUAGGUGAGGCCG
UGGCCAAACGCUUCCACCUACCAGGCAUCCGCCAGGGCUACGGCCUGAC
AGAAACAACCAGCGCCAUUCUGAUCACCCCCGAAGGGGACGACAAGCCU
GGCGCAGUAGGCAAGGUGGUGCCCUUCUUCGAGGCUAAGGUGGUGGACU
UGGACACCGGUAAGACACUGGGUGUGAACCAGCGCGGCGAGCUGUGCGU
CCGUGGCCCCAUGAUCAUGAGCGGCUACGUUAACAACCCCGAGGCUACA
AACGCUCUCAUCGACAAGGACGGCUGGCUGCACAGCGGCGACAUCGCCU
ACUGGGACGAGGACGAGCACUUCUUCAUCGUGGACCGGCUGAAGAGCCU
GAUCAAAUACAAGGGCUACCAGGUAGCCCCAGCCGAACUGGAGAGCAUC
CUGCUGCAACACCCCAACAUCUUCGACGCCGGGGUCGCCGGCCUGCCCG
ACGACGAUGCCGGCGAGCUGCCCGCCGCAGUCGUCGUGCUGGAACACGG
UAAAACCAUGACCGAGAAGGAGAUCGUGGACUAUGUGGCCAGCCAGGUU
ACAACCGCCAAGAAGCUGCGCGGUGGUGUUGUGUUCGUGGACGAGGUGC
CUAAAGGACUGACCGGCAAGUUGGACGCCCGCAAGAUCCGCGAGAUUCU
CAUUAAGGCCAAGAAGGGCGGCAAGAUCGCCGUGUAY -continued

X =
GGGAUCCUACC
(SEQ ID NO: 2)

Y =
UUUGAAUU
(SEQ ID NO: 3)

Next, 0.25 mg of the FFL mRNA was denatured by heating it at 70° C. for 5 minutes using a heat block. A 3 mL volume of an aqueous buffered solution (10 mM citrate/150 mM NaCl, pH 4.5) was prepared and heated in an RNase-Free conical tube by placing the tube in a heated water bath, and into which was followed by the instant addition of the FFL mRNA into the heated aqueous buffered solution to achieve a final FFL mRNA concentration of 0.25 mg/3 mL.

All mRNA concentrations were determined via the Ribogreen assay (Invitrogen). Encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

To prepare the lipid nanoparticles, aliquots of 50 mg/mL ethanolic solutions of HGT4002, DOPE, cholesterol and DMG-PEG2000 were mixed as indicated in Table 3 below, heated to ensure dissolution and diluted with ethanol. The resulting lipid solution is suitable for 0.25 mg mRNA at N/P ratio of 4.

TABLE 3

| Lipid Components | Molar Ratio | MW | µmol | Weight (mg) | Volume (µL) |
| --- | --- | --- | --- | --- | --- |
| DMG-PEG2000 | 6 | 2509.19 | 1.04 | 2.6 | 52.2 |
| HGT4002 | 18 | 506 | 3.12 | 1.6 | 31.6 |
| CHOL | 20 | 386.65 | 3.47 | 1.3 | 26.8 |
| DOPE | 56 | 744.03 | 9.71 | 7.2 | 144.4 |
| Total | 100 | — | 17.33 | 12.8 | 255.0 |

0.5 mL of the ethanolic lipid solution was injected rapidly into the heated (70° C.) aqueous mRNA/buffer solution, shaken and the resulting suspension quickly returned to the 70° C. water bath. The resulting nanoparticle suspension was concentrated, re-suspended in a sodium borate buffer (pH 8.0), passed through MUSTANG Q membranes (Pall Life Sciences), was filtered and diafiltrated with 1× PBS (pH 7.4) and further concentrated. The average Zeta potential of the resulting lipid nanoparticles was 25.7 mV.

A 0.1M stock solution comprising the reducing agent tris (2-carboxyethyl)phosphine (TCEP) was prepared by dissolving 28.7 mg TCEP in 1 mL of water. The lipid nanoparticles were then exposed to aqueous solutions comprising the TCEP and the Zeta potential of the lipid nanoparticle assessed. Exposure of the lipid nanoparticles to 19.5 µL (5×) of a TCEP solution for five minutes caused the Zeta potential of the lipid nanoparticle to increase to 26.1 mV. Exposure of the lipid nanoparticles to 19.5 µL (5×) of a TCEP solution for two hours caused the Zeta potential of the lipid nanoparticle to be reduced to 14.5 mV. Exposure of the lipid nanoparticles to 19.5 µL (5×) of a TCEP solution for four hours caused the Zeta potential of the lipid nanoparticle to be reduced to 5.65 mV. It is likely that the concentration of the TCEP solution and the duration of exposure contributed to the observed changes in the Zeta potential observed in a relatively short period of time.

The foregoing supports the conclusion that upon exposure to a reducing agent, the charge (i.e., Zeta potential) of HGT4002-based lipid nanoparticles can be modulated, and in certain instances neutralized.

Example 4

The present example illustrates that HGT4002-based lipid nanoparticles may be reductively neutralized after having been loaded with mRNA polynucleotide constructs. The HGT4002-based lipid nanoparticles were formed via standard ethanol injection methods as described below. (Ponsa, et al., *Int. J. Pharm.* (1993) 95: 51-56.) Ethanolic stock solutions of the lipids were prepared ahead of time at a concentration of 50 mg/mL and stored at −20° C.

Codon-optimized firefly luciferase (CO-FFL) mRNA was synthesized by in vitro transcription from a plasmid DNA template encoding the gene, which was followed by the addition of a 5' cap structure (Cap1) (Fechter, P. et al., *J. Gen. Virology* (2005) 86: 1239-1249) and a 3' poly(A) tail of approximately 200 nucleotides in length as determined by gel electrophoresis. The 5' and 3' untranslated regions present in each mRNA product are represented as X and Y, respectively in SEQ ID NO: 1, as indicated below.

Codon-Optimized Firefly Luciferase (FFL) mRNA:
SEQ ID NO: 1
XAUGGAAGAUGCCAAAAACAUUAAGAAGGGCCCAGCGCCAUUCUACCCA

CUCGAAGACGGGACCGCCGGCGAGCAGCUGCACAAAGCCAUGAAGCGCU

ACGCCCUGGUGCCCGGCACCAUCGCCUUUACCGACGCACAUAUCGAGGU

GGACAUUACCUACGCCGAGUACUUCGAGAUGAGCGUUCGGCUGGCAGAA

GCUAUGAAGCGCUAUGGGCUGAAUACAAACCAUCGGAUCGUGGUGUGCA

GCGAGAAUAGCUUGCAGUUCUUCAUGCCCGUGUUGGGUGCCCUGUUCAU

CGGUGUGGCUGUGGCCCCAGCUAACGACAUCUACAACGAGCGCGAGCUG

CUGAACAGCAUGGGCAUCAGCCAGCCCACCGUCGUAUUCGUGAGCAAGA

AAGGGCUGCAAAAGAUCCUCAACGUGCAAAAGAAGCUACCGAUCAUACA

AAAGAUCAUCAUCAUGGAUAGCAAGACCGACUACCAGGGCUUCCAAAGC

AUGUACACCUUCGUGACUUCCCAUUUGCCACCCGGCUUCAACGAGUACG

ACUUCGUGCCCGAGAGCUUCGACCGGGACAAAACCAUCGCCCUGAUCAU

GAACAGUAGUGGCAGUACCGGAUUGCCCAAGGGCGUAGCCCUACCGCAC

CGCACCGCUUGUGUCCGAUUCAGUCAUGCCCGCGACCCCAUCUUCGGCA

ACCAGAUCAUCCCCGACACCGCUAUCCUCAGCGUGGUGCCAUUUCACCA

CGGCUUCGGCAUGUUCACCACGCUGGGCUACUUGAUCUGCGGCUUUCGG

GUCUGCUCAUGUACCGCUUCGAGGAGGAGCUAUUCUUGCGCAGCUUGC

AAGACUAUAAGAUUCAAUCUGCCCUGCUGGUGCCCACACUAUUUAGCUU

CUUCGCUAAGAGCACUCUCAUCGACAAGUACGACCUAAGCAACUUGCAC

GAGAUCGCCAGCGGCGGGGCGCCGCUCAGCAAGGAGGUAGGUGAGGCCG

UGGCCAAACGCUUCCACCUACCAGGCAUCCGCCAGGGCUACGGCCUGAC

AGAAACAACCAGCGCCAUUCUGAUCACCCCCGAAGGGGACGACAAGCCU

GGCGCAGUAGGCAAGGUGGUGCCCUUCUUCGAGGCUAAGGUGGUGGACU

UGGACACCGGUAAGACACUGGGUGUGAACCAGCGCGGCGAGCUGUGCGU

```
-continued
CCGUGGCCCCAUGAUCAUGAGCGGCUACGUUAACAACCCCGAGGCUACA

AACGCUCUCAUCGACAAGGACGGCUGGCUGCACAGCGGCGACAUCGCCU

ACUGGGACGAGGACGAGCACUUCUUCAUCGUGGACCGGCUGAAGAGCCU

GAUCAAAUACAAGGGCUACCAGGUAGCCCCAGCCGAACUGGAGAGCAUC

CUGCUGCAACACCCCAACAUCUUCGACGCCGGGGUCGCCGGCCUGCCCG

ACGACGAUGCCGGCGAGCUGCCCGCCGCAGUCGUCGUGCUGGAACACGG

UAAAACCAUGACCGAGAAGGAGAUCGUGGACUAUGUGGCCAGCCAGGUU

ACAACCGCCAAGAAGCUGCGCGGUGGUGUUGUGUUCGUGGACGAGGUGC

CUAAAGGACUGACCGGCAAGUUGGACGCCCGCAAGAUCCGCGAGAUUCU

CAUUAAGGCCAAGAAGGGCGGCAAGAUCGCCGUGUAY

X =
                                              (SEQ ID NO: 2)
GGGAUCCUACC

Y =
                                              (SEQ ID NO: 3)
UUUGAAUU
```

Next, 0.25 mg of the FFL mRNA was denatured by heating it at 70° C. for 5 minutes using a heat block. An 11 mL volume of an aqueous buffered solution (10 mM citrate/150 mM NaCl, pH 4.5) was prepared and heated in a 50 mL RNase-Free conical tube by placing the tube in a heated water bath, and into which was followed by the instant addition of the denatured CO-FFL mRNA into the heated aqueous buffered solution to achieve a final FFL mRNA concentration of 1 mg/11 mL.

All mRNA concentrations were determined via the Ribogreen assay (Invitrogen). Encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

To prepare the lipid nanoparticles, aliquots of 50 mg/mL ethanolic solutions of HGT4002, DOPE, cholesterol and DMG-PEG2000 were mixed as indicated in Table 4 below, heated to ensure dissolution and diluted with ethanol. The resulting lipid solution is suitable for 0.25 mg mRNA at N/P ratio of 4.

TABLE 4

| Lipid Components | Molar Ratio | MW | µmol | Weight (mg) | Volume (µL) |
|---|---|---|---|---|---|
| DMG-PEG2000 | 10 | 2509.19 | 2.50 | 6.3 | 125.5 |
| HGT4002 | 50 | 506 | 12.50 | 6.3 | 126.5 |
| CHOL | 20 | 386.65 | 5.0 | 1.9 | 38.7 |
| DOPE | 20 | 744.03 | 5.0 | 3.7 | 74.4 |
| Total | 100 | — | 25.00 | 18.3 | 365.0 |

3.0 mL of the ethanolic lipid solution was injected rapidly into the heated (70° C.) aqueous mRNA/buffer solution, shaken and the resulting suspension quickly returned to the 70° C. water bath. The resulting nanoparticle suspension was concentrated, re-suspended in a sodium borate buffer (pH 8.0), passed through MUSTANG Q membranes (Pall Life Sciences), was filtered and diafiltrated with 1× PBS (pH 7.4) and further concentrated. The $Z_{ave}$ of the resulting lipid nanoparticles was 58.40 nm ($Dv_{(50)}$=44.7 nm; $Dv_{(90)}$=65.1 nm) and the average Zeta potential was +7.8 mV. Encapsulation of mRNA was calculated by performing the Ribogreen assay with and without the presence of 0.1% Triton-X 100 and determined to be 88.56%.

A 0.1M stock solution comprising the reducing agent tris (2-carboxyethyl)phosphine (TCEP) was prepared by dissolving 28.7 mg TCEP in 1 mL of water. The lipid nanoparticles were then exposed to aqueous solutions comprising the TCEP and the Zeta potential of the lipid nanoparticle assessed. Exposure of the lipid nanoparticles to 39 µL (10×) of a TCEP solution for three hours caused the Zeta potential of the lipid nanoparticle to decrease to −17.1 mV. Exposure of the lipid nanoparticles to 19.5 µL (5×) of a TCEP solution for one hour caused the Zeta potential of the lipid nanoparticle to be reduced to −4.15 mV. The foregoing supports the conclusion that upon exposure to a reducing agent, the charge (i.e., Zeta potential) of HGT4002-based lipid nanoparticles can be modulated, and in certain instances neutralized.

Example 5

The present example illustrates that HGT4002-based lipid nanoparticles may be reductively neutralized after having been loaded with mRNA polynucleotide constructs. The HGT4002-based lipid nanoparticles were formed via standard ethanol injection methods as described below. (Ponsa, et al., Int. J Pharm. (1993) 95: 51-56.) Ethanolic stock solutions of the lipids were prepared ahead of time at a concentration of 50 mg/mL and stored at −20° C.

Codon-optimized firefly luciferase (CO-FFL) mRNA was synthesized by in vitro transcription from a plasmid DNA template encoding the gene, which was followed by the addition of a 5' cap structure (Cap1) (Fechter, P. et al., J. Gen. Virology (2005) 86: 1239-1249) and a 3' poly(A) tail of approximately 200 nucleotides in length as determined by gel electrophoresis. The 5' and 3' untranslated regions present in each mRNA product are represented as X and Y, respectively in SEQ ID NO: 1, as listed below.

```
Codon-Optimized Firefly Luciferase (FFL) mRNA:
                                              SEQ ID NO: 1
XAUGGAAGAUGCCAAAAACAUUAAGAAGGGCCCAGCGCCAUUCUACCCA

CUCGAAGACGGGACCGCCGGCGAGCAGCUGCACAAAGCCAUGAAGCGCU

ACGCCCUGGUGCCCGGCACCAUCGCCUUUACCGACGCACAUAUCGAGGU

GGACAUUACCUACGCCGAGUACUUCGAGAUGAGCGUUCGGCUGGCAGAA

GCUAUGAAGCGCUAUGGGCUGAAUACAAACCAUCGGAUCGUGGUGUGCA

GCGAGAAUAGCUUGCAGUUCUUCAUGCCCGUGUUGGGUGCCCUGUUCAU

CGGUGUGGCUGUGGCCCCAGCUAACGACAUCUACAACGAGCGCGAGCUG

CUGAACAGCAUGGGCAUCAGCCAGCCCACCGUCGUAUUCGUGAGCAAGA

AAGGGCUGCAAAAGAUCCUCAACGUGCAAAAGAAGCUACCGAUCAUACA

AAAGAUCAUCAUCAUGGAUAGCAAGACCGACUACCAGGGCUUCCAAAGC

AUGUACACCUUCGUGACUUCCCAUUUGCCACCCGGCUUCAACGAGUACG

ACUUCGUGCCCGAGAGCUUCGACCGGGACAAAACCAUCGCCCUGAUCAU

GAACAGUAGUGGCAGUACCGGAUUGCCCAAGGGCGUAGCCCUACCGCAC

CGCACCGCUUGUGUCCGAUUCAGUCAUGCCCGCGACCCCAUCUUCGGCA

ACCAGAUCAUCCCCGACACCGCUAUCCUCAGCGUGGUGCCAUUUCACCA
```

-continued

```
CGGCUUCGGCAUGUUCACCACGCUGGGCUACUUGAUCUGCGGCUUUCGG

GUCGUGCUCAUGUACCGCUUCGAGGAGGAGCUAUUCUUGCGCAGCUUGC

AAGACUAUAAGAUUCAAUCUGCCCUGCUGGUGCCCACACUAUUUAGCUU

CUUCGCUAAGAGCACUCUCAUCGACAAGUACGACCUAAGCAACUUGCAC

GAGAUCGCCAGCGGCGGGGCGCCGCUCAGCAAGGAGGUAGGUGAGGCCG

UGGCCAAACGCUUCCACCUACCAGGCAUCCGCCAGGGCUACGGCCUGAC

AGAAACAACCAGCGCCAUUCUGAUCACCCCCGAAGGGGACGACAAGCCU

GGCGCAGUAGGCAAGGUGGUGCCCUUCUUCGAGGCUAAGGUGGUGGACU

UGGACACCGGUAAGACACUGGGUGUGAACCAGCGCGGCGAGCUGUGCGU

CCGUGGCCCAUGAUCAUGAGCGGCUACGUUAACAACCCCGAGGCUACA

AACGCUCUCAUCGACAAGGACGGCUGGCUGCACAGCGGCGACAUCGCCU

ACUGGGACGAGGACGAGCACUUCUUCAUCGUGGACCGGCUGAAGAGCCU

GAUCAAAUACAAGGGCUACCAGGUAGCCCCAGCCGAACUGGAGAGCAUC

CUGCUGCAACACCCCAACAUCUUCGACGCCGGGGUCGCCGGCCUGCCCG

ACGACGAUGCCGGCGAGCUGCCCGCCGCAGUCGUCGUGCUGGAACACGG

UAAAACCAUGACCGAGAAGGAGAUCGUGGACUAUGUGGCCAGCCAGGUU

ACAACCGCCAAGAAGCUGCGCGGUGGUGUUGUGUUCGUGGACGAGGUGC

CUAAAGGACUGACCGGCAAGUUGGACGCCCGCAAGAUCCGCGAGAUUCU

CAUUAAGGCCAAGAAGGGCGGCAAGAUCGCCGUGUAY

X =
                                        (SEQ ID NO: 2)
GGGAUCCUACC

Y =
                                        (SEQ ID NO: 3)
UUUGAAUU
```

Next, 0.25 mg of the FFL mRNA was denatured by heating it at 70° C. for 5 minutes using a heat block. An 11 mL volume of an aqueous buffered solution (10 mM citrate/150 mM NaCl, pH 4.5) was prepared and heated in a 50 mL RNase-Free conical tube by placing the tube in a heated water bath, and into which was followed by the instant addition of the denatured CO-FFL mRNA into the heated aqueous buffered solution to achieve a final FFL mRNA concentration of 1 mg/11 mL.

All mRNA concentrations were determined via the Ribogreen assay (Invitrogen). Encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

To prepare the lipid nanoparticles, aliquots of 50 mg/mL ethanolic solutions of HGT4002, DOPE, cholesterol and DMG-PEG2000 were mixed as indicated below in Table 5, heated to ensure dissolution and diluted with ethanol. The resulting lipid solution is suitable for 0.25 mg mRNA at N/P ratio of 4.

TABLE 5

| Lipid Components | Molar Ratio | MW | μmol | Weight (mg) | Volume (μL) |
| --- | --- | --- | --- | --- | --- |
| DMG-PEG2000 | 10 | 2509.19 | 2.50 | 6.3 | 125.5 |
| HGT4002 | 50 | 506 | 12.50 | 6.3 | 126.5 |
| CHOL | 20 | 386.65 | 5.0 | 1.9 | 38.7 |
| DOPE | 20 | 744.03 | 5.0 | 3.7 | 74.4 |
| Total | 100 | — | 25.00 | 18.3 | 365.0 |
| Ethanol (additional) | — | — | — | — | 2635.0 |
| Final Volume | | | | | 3000.0 |

3.0 mL of the ethanolic lipid solution was injected rapidly into the heated (70° C.) aqueous mRNA/buffer solution, shaken and the resulting suspension quickly returned to the 70° C. water bath. The resulting nanoparticle suspension was concentrated, re-suspended in a sodium borate buffer (pH 8.0), passed through MUSTANG Q membranes (Pall Life Sciences), was filtered and diafiltrated with 1× PBS (pH 7.4) and further concentrated. The $Z_{ave}$ of the resulting lipid nanoparticles was 66.43 nm ($Dv_{(50)}$=38.7 nm; $Dv_{(90)}$=67.9 nm) and the average Zeta potential was approximately 25.0 mV. Encapsulation of mRNA was calculated by performing the Ribogreen assay with and without the presence of 0.1% Triton-X 100 and determined to be 70.79%.

A 0.1M stock solution comprising the reducing agent tris (2-carboxyethyl)phosphine (TCEP) was prepared by dissolving 28.7 mg TCEP in 1 mL of water. The lipid nanoparticles were then exposed to aqueous solutions comprising the TCEP and the Zeta potential of the lipid nanoparticle assessed. Exposure of the lipid nanoparticles to 19.5 μL (5×) of a TCEP solution for one hour caused the Zeta potential of the lipid nanoparticle to be reduced to 14.9 mV. The foregoing supports the conclusion that upon exposure to a reducing agent, the charge (i.e., Zeta potential) of HGT4002-based lipid nanoparticles can be modulated, and in certain instances neutralized.

We claim:

1. A composition comprising a lipid nanoparticle having an overall neutral surface charge and encapsulating negatively charged mRNA, wherein said lipid nanoparticle is made by a method comprising the steps of:
   (a) encapsulating said negatively charged mRNA within a lipid nanoparticle, wherein the lipid nanoparticle comprises:
      a cationic lipid, the cationic lipid comprising a polar head-group bound to a lipophilic tail-group via a linker group, the polar head-group being exposed on the surface of the lipid nanoparticle, and the linker group being susceptible to chemical or enzymatic cleavage;
      a PEG-modified lipid;
      one or more non-cationic lipids that is zwitterionic or anionic; and
      one or more non-cationic lipids that is neutral; and
   (b) exposing the lipid nanoparticle to chemical or enzymatic cleavage thereby releasing the polar head-group from the surface of the lipid nanoparticle to provide an overall neutral surface charge to the lipid nanoparticle.

2. The composition of claim 1, wherein the encapsulation efficiency of step (a) is at least 75%.

3. The composition of claim 2, wherein the encapsulation efficiency is at least 90%.

4. The composition of claim 1, wherein following step (b) the lipid nanoparticle has a surface charge or zeta potential of about −2.5 to about +2.5 mV.

5. The composition of claim 1, wherein the cationic lipid with the releasable polar head group is represented by the structural formula:

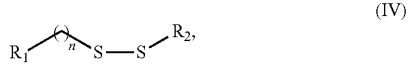

(IV)

or a pharmaceutically acceptable salt thereof, wherein:
$R_1$ is selected from the group consisting of imidazole; guanidinium; imine; enamine; amino; an alkyl amino optionally-substituted with alkyl, halo, alkoxy, hydroxyl, amino, aryl, ether, ester, or amide; or a pyridyl optionally substituted with alkyl, halo, alkoxy, hydroxyl, amino, aryl, ether, ester, or amide;
$R_2$ is selected from the group consisting of alkyl, alkenyl, acyl, pyridyl,

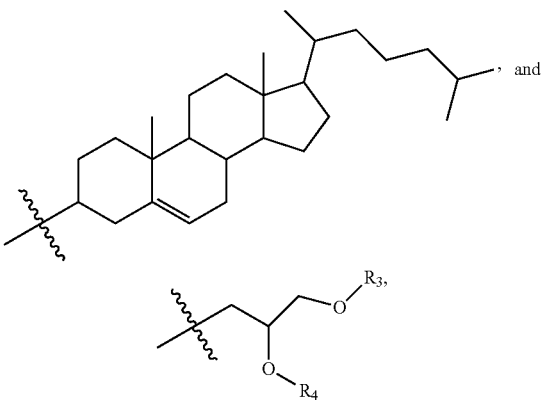

each optionally substituted with alkyl, halo, alkoxy, hydroxyl, amino, aryl, ether, ester, nitro, or amide;
$R_3$ and $R_4$ are each independently selected from the group consisting of $C_5$-$C_{20}$ alkyl, $C_6$-$C_{20}$ alkenyl, and $C_6$-$C_{20}$ acyl, each optionally substituted with alkyl, halo, alkoxy, hydroxyl, amino, aryl, ether, ester, or amide; and
n is zero or any positive integer; and
wherein the modulating step comprises exposing the lipid nanoparticle to a reducing agent thereby cleaving the linker group and releasing the polar head-group from the lipophilic tail-group.

6. The composition of claim 1, wherein the cationic lipid is selected from the group consisting of:

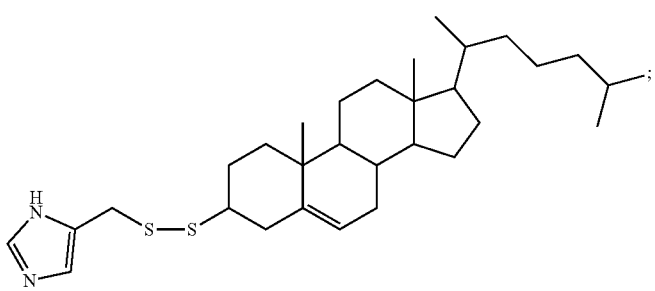

(HGT4001)

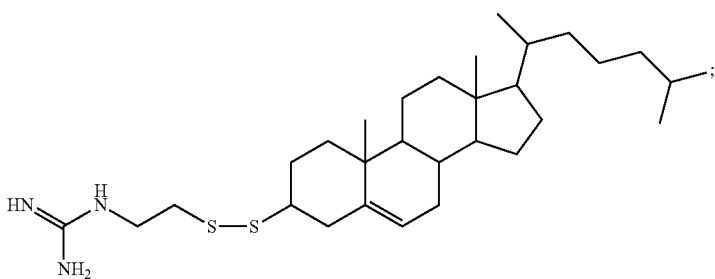

(HGT4002)

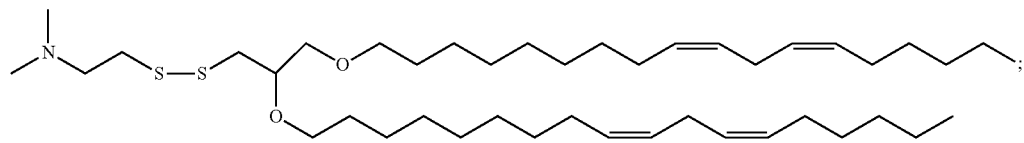
(HGT4003)

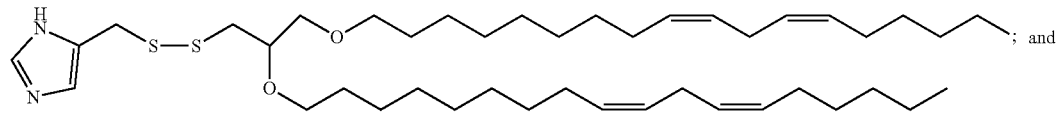
(HGT4004)

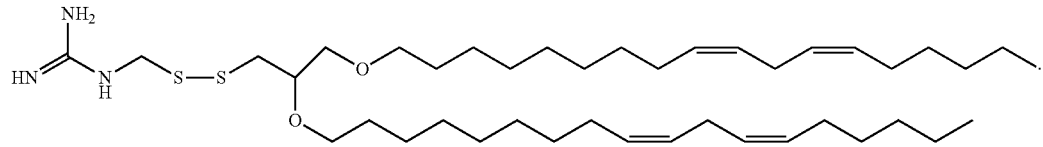
(HGT4005)

7. The composition of claim 1, wherein the composition comprises the following structure after the modulating step:

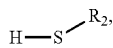
(VI)

or a pharmaceutically acceptable salt thereof,
wherein:
$R_2$ is selected from the group consisting of alkyl, alkenyl, acyl, pyridyl,

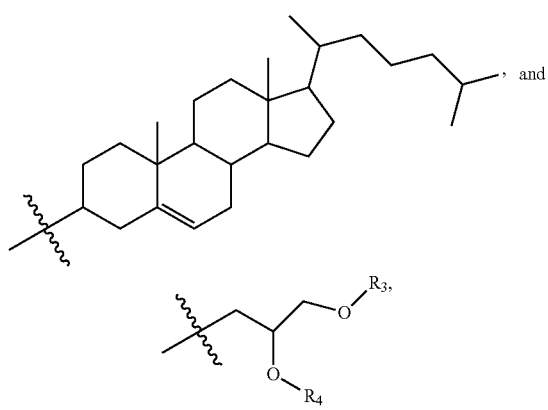

each optionally substituted with alkyl, halo, alkoxy, hydroxyl, amino, aryl, ether, ester, nitro, or amide;
$R_3$ and $R_4$ are each independently selected from the group consisting of $C_6$-$C_{20}$ alkyl, $C_6$-$C_{20}$ alkenyl, and $C_6$-$C_{20}$ acyl, each optionally substituted with alkyl, halo, alkoxy, hydroxyl, amino, aryl, ether, ester, or amide; and
n is zero or any positive integer;
and
wherein the modulating step comprises exposing the lipid nanoparticle to a reducing agent thereby cleaving the linker group and releasing the polar head-group from the lipophilic tail-group.

8. The composition of claim 1, wherein said mRNA encodes ornithine transcarbamylase (OTC), carbamoyl-phosphate synthetase 1 (CPS1), argininosuccinate synthetase (ASS1), argininosuccinate lyase (ASL) or arginase 1 (ARG1).

9. The composition of claim 1, wherein said mRNA encodes an enzyme or protein selected from the group consisting of erythropoietin, human growth hormone, cystic fibrosis transmembrane conductance regulator (CFTR), alpha-L-iduronidase, N-acetylglucosaminidase, alpha-glucosaminide acetyltransferase, N-acetylglucosamine 6-sulfatase, N-acetylgalactosamine-4-sulfatase, galactose-6-sulfate sulfatase, beta-galactosidase, beta-glucuronidase, glucocerebrosidase, heparan sulfamidase, heparin-N-sulfatase, lysosomal acid lipase, acid alpha-glucosidase, arylsulfatase A and hyaluronidase.

10. The composition of claim 1, wherein said one or more non-cationic lipids that is zwitterionic or anionic is: distearoylphosphatidylcholine (DSPC), dioleoylphosphatidylcholine (DOPC), dipalmitoylphosphatidylcholine (DPPC), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), DLPE (1,2-dilauroyl-sn-glycero-3-phosphoethanolamine), DPPS (1,2-dipalmitoyl-sn-glycero-3-phospho-L-serine), 16-O-monomethyl PE, 16-O-dimethyl PE, 18-1-trans PE, 1-stearoyl-2-oleoyl-phosphatidyethanolamine (SOPE), a sphingomyelin, or a mixture thereof.

11. The composition of claim 1, wherein said one or more non-cationic lipids that is neutral comprises cholesterol.

12. A pharmaceutical composition comprising a lipid nanoparticle having an overall neutral surface charge and encapsulating negatively charged mRNA, wherein said lipid nanoparticle is made by a method comprising the steps of:
(a) encapsulating said negatively charged mRNA within a lipid nanoparticle, wherein the lipid nanoparticle comprises:
a cationic lipid, the cationic lipid comprising a polar head-group bound to a lipophilic tail-group via a linker group, the polar head-group being exposed on the surface of the lipid nanoparticle, and the linker group being susceptible to chemical or enzymatic cleavage;
a PEG-modified lipid;

one or more non-cationic lipids that is zwitterionic or anionic; and
one or more non-cationic lipids that is neutral;
and
(b) exposing the surface of the lipid nanoparticle to chemical or enzymatic cleavage thereby releasing the polar head-group from the surface of the lipid nanoparticle to provide an overall neutral surface to the lipid nanoparticle.

13. The pharmaceutical composition of claim 12, wherein the encapsulation efficiency of step (a) is at least 75%.

14. The pharmaceutical composition of claim 13, wherein the encapsulation efficiency is at least 90%.

15. The pharmaceutical composition of claim 12, wherein following step (b) the lipid nanoparticle has a surface charge or zeta potential of about −2.5 to about +2.5 mV.

16. The pharmaceutical composition of claim 12, wherein the cationic lipid with the releasable polar head group is represented by the structural formula:

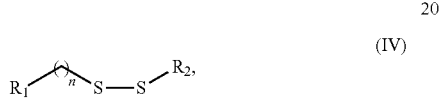
(IV)

or a pharmaceutically acceptable salt thereof,
wherein:
$R_1$ is selected from the group consisting of imidazole; guanidinium; imine; enamine; amino; an alkyl amino optionally-substituted with alkyl, halo, alkoxy, hydroxyl, amino, aryl, ether, ester, or amide; or a pyridyl optionally substituted with alkyl, halo, alkoxy, hydroxyl, amino, aryl, ether, ester, or amide;
$R_2$ is selected from the group consisting of alkyl, alkenyl, acyl, pyridyl,

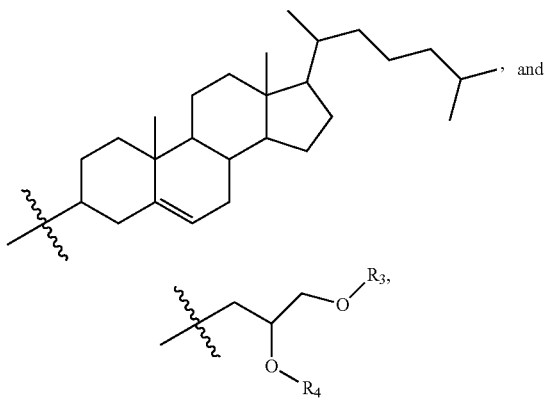

each optionally substituted with alkyl, halo, alkoxy, hydroxyl, amino, aryl, ether, ester, nitro, or amide;
$R_3$ and $R_4$ are each independently selected from the group consisting of $C_5$-$C_{20}$ alkyl, $C_6$-$C_{20}$ alkenyl, and $C_6$-$C_{20}$ acyl, each optionally substituted with alkyl, halo, alkoxy, hydroxyl, amino, aryl, ether, ester, or amide; and
n is zero or any positive integer;
and
wherein the modulating step comprises exposing the lipid nanoparticle to a reducing agent thereby cleaving the linker group and releasing the polar head-group from the lipophilic tail-group.

17. The pharmaceutical composition of claim 12, wherein the cationic lipid is selected from the group consisting of:

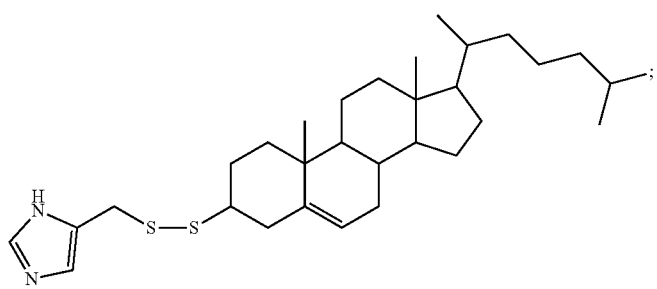
(HGT4001)

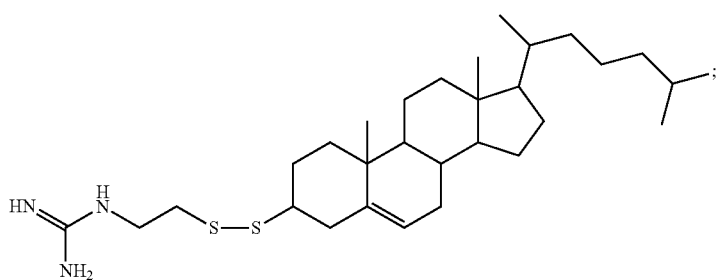
(HGT4002)

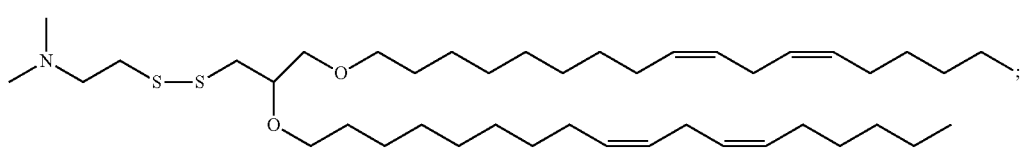
(HGT4003)

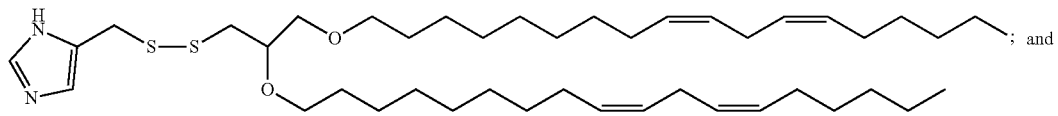
(HGT4004)

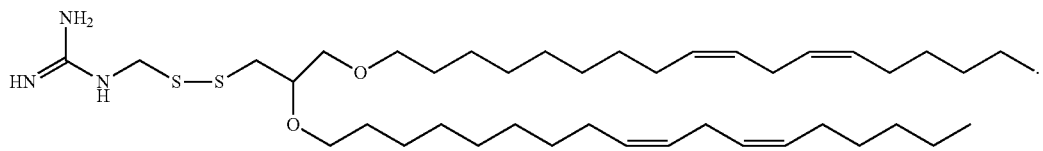
(HGT4005)

18. The pharmaceutical composition of claim 12, wherein the composition comprises the following structure after the modulating step:

$$H-S^{R_2},$$ (VI)

or a pharmaceutically acceptable salt thereof,
wherein:
$R_2$ is selected from the group consisting of alkyl, alkenyl, acyl, pyridyl,

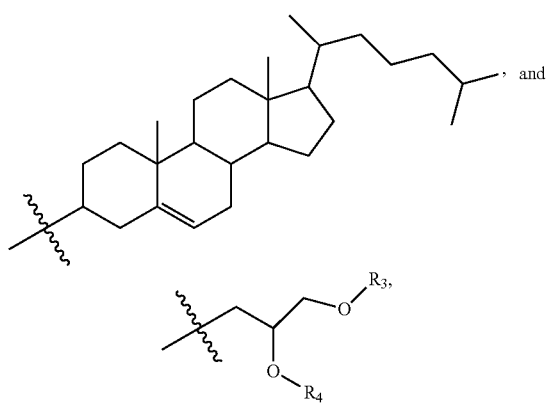

each optionally substituted with alkyl, halo, alkoxy, hydroxyl, amino, aryl, ether, ester, nitro, or amide;
$R_3$ and $R_4$ are each independently selected from the group consisting of $C_6$-$C_{20}$ alkyl, $C_6$-$C_{20}$ alkenyl, and $C_6$-$C_{20}$ acyl, each optionally substituted with alkyl, halo, alkoxy, hydroxyl, amino, aryl, ether, ester, or amide; and
n is zero or any positive integer;
and
wherein the modulating step comprises exposing the lipid nanoparticle to a reducing agent thereby cleaving the linker group and releasing the polar head-group from the lipophilic tail-group.

19. The pharmaceutical composition of claim 12, wherein said mRNA encodes ornithine transcarbamylase (OTC), carbamoyl-phosphate synthetase 1 (CPS1), argininosuccinate synthetase (ASS1), argininosuccinate lyase (ASL) or arginase 1 (ARG1).

20. The pharmaceutical composition of claim 12, wherein said mRNA encodes an enzyme or protein selected from the group of enzymes consisting of erythropoietin, human growth hormone, cystic fibrosis transmembrane conductance regulator (CFTR), alpha-L-iduronidase, N-acetylglucosaminidase, alpha-glucosaminide acetyltransferase, N-acetylglucosamine 6-sulfatase, N-acetylgalactosamine-4-sulfatase, galactose-6-sulfate sulfatase, beta-galactosidase, beta-glucuronidase, glucocerebrosidase, heparan sulfamidase, heparin-N-sulfatase, lysosomal acid lipase, acid alpha-glucosidase, arylsulfatase A and hyaluronidase.

21. The pharmaceutical composition of claim 12, wherein said one or more non-cationic lipids that is zwitterionic or anionic is: distearoylphosphatidylcholine (DSPC), dioleoyl-phosphatidylcholine (DOPC), dipalmitoylphosphatidylcholine (DPPC), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), DLPE (1,2-dilauroyl-sn-glycero-3-phosphoethanolamine), DPPS (1,2-dipalmitoyl-sn-glycero-3-phospho-L-serine), 16-O-monomethyl PE, 16-O-dimethyl PE, 18-1-trans PE, 1-stearoyl-2-oleoyl-phosphatidyethanolamine (SOPE), a sphingomyelin, or a mixture thereof.

22. The pharmaceutical composition of claim 12, wherein said one or more non-cationic lipids that is neutral comprises cholesterol.

* * * * *

SEQUENCE LISTING

<160> NUMBER OF SEQ ID NOS: 3

<210> SEQ ID NO 1
<211> LENGTH: 1671
<212> TYPE: RNA
<213> ORGANISM: Photinus pyralis

<400> SEQUENCE: 1
gggauccuac cauggaagau gccaaaaaca uuaagaaggg cccagcgcca uucuacccac      60
ucgaagacgg gaccgccggc gagcagcugc acaaagccau gaagcgcuac gcccuggugc     120

-continued

| | |
|---|---|
| ccggcaccau cgccuuuacc gacgcacaua ucgaggugga cauuaccuac gccgaguacu | 180 |
| ucgagaugag cguucggcug gcagaagcua ugaagcgcua ugggcugaau acaaaccauc | 240 |
| ggaucguggu gugcagcgag aauagcuugc aguucuucau gcccguguug ggugcccugu | 300 |
| ucaucgugu ggcuguggcc ccagcuaacg acaucuacaa cgagcgcgag cugcugaaca | 360 |
| gcaugggcau cagccagccc accgucguau ucgagcaa gaaagggcug caaaagaucc | 420 |
| ucaacgugca aagaagcua ccgaucauac aaaagaucau caucauggau agcaagaccg | 480 |
| acuaccaggg cuuccaaagc auguacaccu ucgugacuuc ccauuugcca ccggcuuca | 540 |
| acgaguacga cuucgugccc gagagcuucg accgggacaa aaccaucgcc cugaucauga | 600 |
| acaguagugg caguaccgga uugcccaagg gcguagcccu accgcaccgc accgcuugug | 660 |
| uccgauucag ucaugcccgc gaccccaucu ucggcaacca gaucauccc gacaccgcua | 720 |
| uccucagcgu ggugccauuu caccacggcu ucggcauguu caccacgcug ggcuacuuga | 780 |
| ucugcggcuu ucgggucgug cucauguacc gcuucgagga ggagcuauuc uugcgcagcu | 840 |
| ugcaagacua uaagauucaa ucugcccugc uggugcccac acuauuuagc uucuucgcua | 900 |
| agagcacucu caucgacaag uacgaccuaa gcaacuugca cgagaucgcc agcggcgggg | 960 |
| cgccgcucag caaggaggua ggugaggccg uggccaaacg cuuccaccua ccaggcaucc | 1020 |
| gccagggcua cggccugaca gaaacaacca gcgccauucu gaucacccc gaaggggacg | 1080 |
| acaagccugg cgcaguaggc aaggugguge ccuucuucga ggcuaaggug guggacuugg | 1140 |
| acaccgguaa gacacugggu gugaaccagc gcggcgagcu gugcgaccgu ggccccauga | 1200 |
| ucaugagcgg cuacguuaac aaccccgagg cuacaaacgc ucucaucgac aaggacggcu | 1260 |
| ggcugcacag cggcgacauc gccuacuggg acgaggacga gcacuucuuc aucguggacc | 1320 |
| ggcugaagag ccugaucaaa uacaagggcu accagguagc cccagccgaa cuggagagca | 1380 |
| uccugcugca acaccccaac aucuucgacg ccggggucgc cggccugccc gacgacgaug | 1440 |
| ccggcgagcu gcccgccgca gucgucgugc uggaacacgg uaaaaccaug accgagaagg | 1500 |
| agaucgugga cuaugguggcc agccagguua caaccgccaa gaagcugcgc gguggguguug | 1560 |
| uguucgugga cgaggugccu aaaggacuga ccggcaaguu ggacgcccgc aagauccgcg | 1620 |
| agauucucau uaaggccaag aagggcggca agaucgccgu guauuugaau u | 1671 |

<210> SEQ ID NO 2
<211> LENGTH: 11
<212> TYPE: RNA
<213> ORGANISM: Homo sapiens

<400> SEQUENCE: 2
gggauccuac c                                                            11

<210> SEQ ID NO 3
<211> LENGTH: 8
<212> TYPE: RNA
<213> ORGANISM: Homo sapiens

<400> SEQUENCE: 3 uuugaauu                                                                8